United States Patent
Gregory

(10) Patent No.: US 11,224,447 B2
(45) Date of Patent: Jan. 18, 2022

(54) DRILL TAP DILATOR

(71) Applicant: SPINE WAVE, INC., Shelton, CT (US)

(72) Inventor: Zachary Gregory, St. Louis, MO (US)

(73) Assignee: SPINE WAVE, INC., Shelton, CT (US)

( * ) Notice: Subject to any disclaimer, the term of this patent is extended or adjusted under 35 U.S.C. 154(b) by 162 days.

(21) Appl. No.: 16/787,220

(22) Filed: Feb. 11, 2020

(65) Prior Publication Data
US 2020/0253619 A1 Aug. 13, 2020

Related U.S. Application Data

(60) Provisional application No. 62/804,947, filed on Feb. 13, 2019.

(51) Int. Cl.
| | | |
|---|---|---|
| *A61B 17/17* | (2006.01) | |
| *A61B 17/16* | (2006.01) | |
| *A61M 29/00* | (2006.01) | |
| *A61F 2/46* | (2006.01) | |
| *A61F 2/44* | (2006.01) | |

(52) U.S. Cl.
CPC ...... *A61B 17/1757* (2013.01); *A61B 17/1633* (2013.01); *A61F 2/446* (2013.01); *A61F 2/4611* (2013.01); *A61M 29/00* (2013.01)

(58) Field of Classification Search
CPC ..... A61B 17/02; A61B 17/0218; A61B 17/17; A61B 17/1739; A61B 17/1757; A61B 17/34; A61B 17/3417; A61B 17/3421; A61B 17/3423; A61B 2017/3443; A61M 29/00
See application file for complete search history.

(56) References Cited

U.S. PATENT DOCUMENTS

| | | | |
|---|---|---|---|
| 4,969,888 A | 11/1990 | Scholten et al. | |
| 5,015,247 A * | 5/1991 | Michelson | A61F 2/446 606/247 |
| 5,954,671 A | 9/1999 | O'Neill | |
| 6,241,729 B1 | 6/2001 | Estes et al. | |
| 6,428,541 B1 * | 8/2002 | Boyd | A61F 2/4611 606/86 A |
| 6,450,992 B1 * | 9/2002 | Cassidy, Jr. | A61B 17/3421 604/164.01 |
| 7,419,496 B2 * | 9/2008 | Staudner | A61B 17/3496 606/185 |
| 8,900,193 B2 * | 12/2014 | Paul | A61B 17/3478 604/164.12 |

(Continued)

*Primary Examiner* — Eric S Gibson
(74) *Attorney, Agent, or Firm* — Hoffmann & Baron, LLP

(57) ABSTRACT

A drill tap dilator comprises a dilator body having a central lumen extending therethrough, an elongate sleeve slidably received with the lumen, and a control knob coupled to the sleeve. The control knob is movable rotatably and axially relative to the dilator body. The sleeve includes docking teeth that are extendable from a retracted position within the body lumen to a deployed position outside the body lumen upon rotation of the control knob relative to the dilator body in one rotational direction. Adjustment of the length of drill tap dilator is allowed upon rotation of the control knob in an opposite rotational direction relative to the dilator body and manual axial movement of the control knob relative to the dilator body.

26 Claims, 26 Drawing Sheets

(56) References Cited

U.S. PATENT DOCUMENTS

| | | | |
|---|---|---|---|
| 9,119,645 B2* | 9/2015 | McBride | A61B 17/1757 |
| 9,848,922 B2* | 12/2017 | Tohmeh | A61B 34/25 |
| 9,855,063 B2* | 1/2018 | Feibel | A61B 17/1717 |
| 9,962,184 B2* | 5/2018 | Paul | A61M 29/00 |
| 2005/0234495 A1* | 10/2005 | Schraga | A61B 5/151 |
| | | | 606/181 |
| 2008/0086144 A1* | 4/2008 | Zander | A61B 17/17 |
| | | | 606/96 |
| 2015/0150592 A1* | 6/2015 | Paul | A61B 17/3478 |
| | | | 604/104 |
| 2019/0231369 A1* | 8/2019 | Cardon | A61B 17/1684 |
| 2019/0342648 A1 | 11/2019 | Lee | |
| 2020/0253619 A1* | 8/2020 | Gregory | A61B 17/1757 |

* cited by examiner

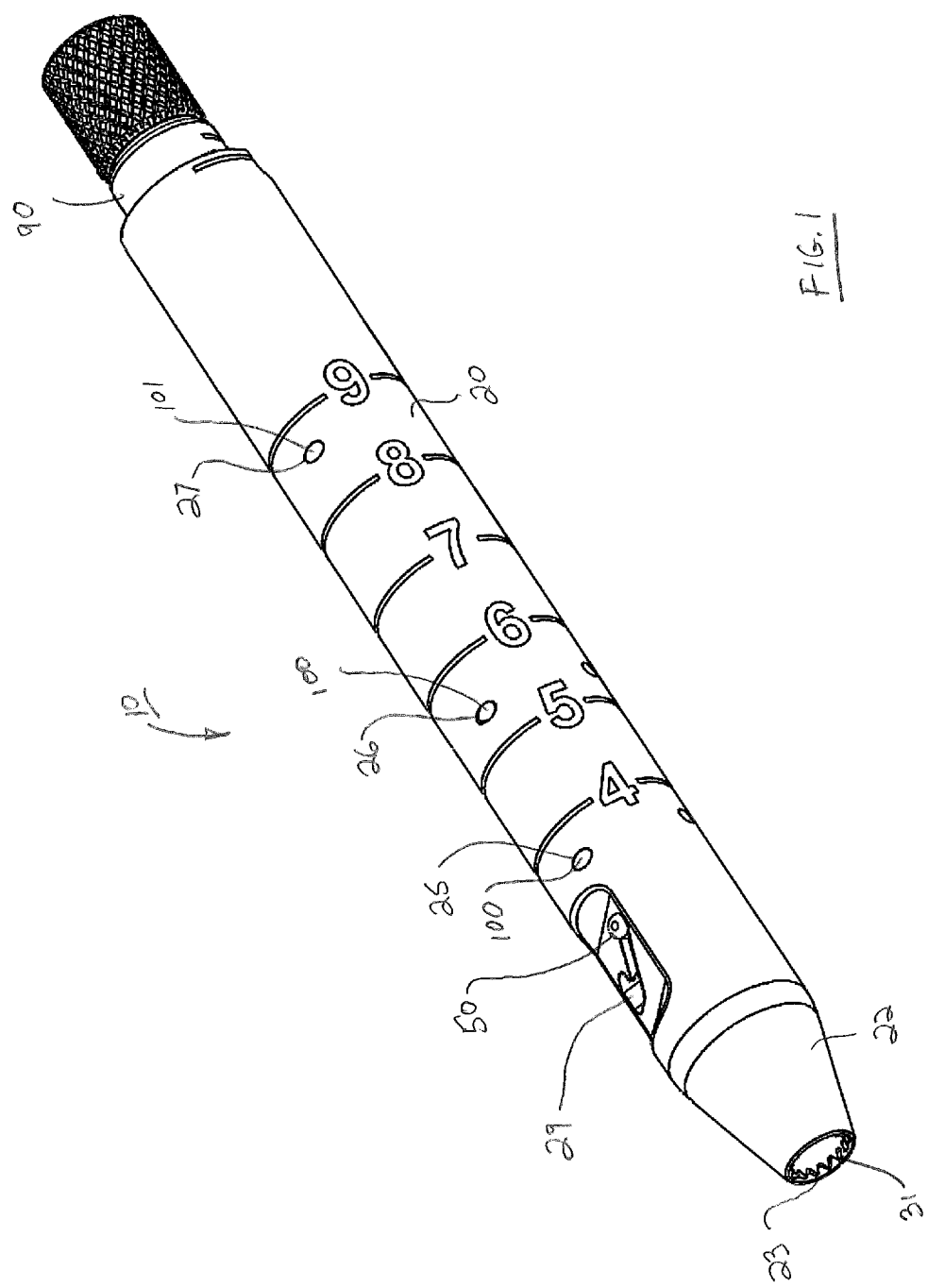

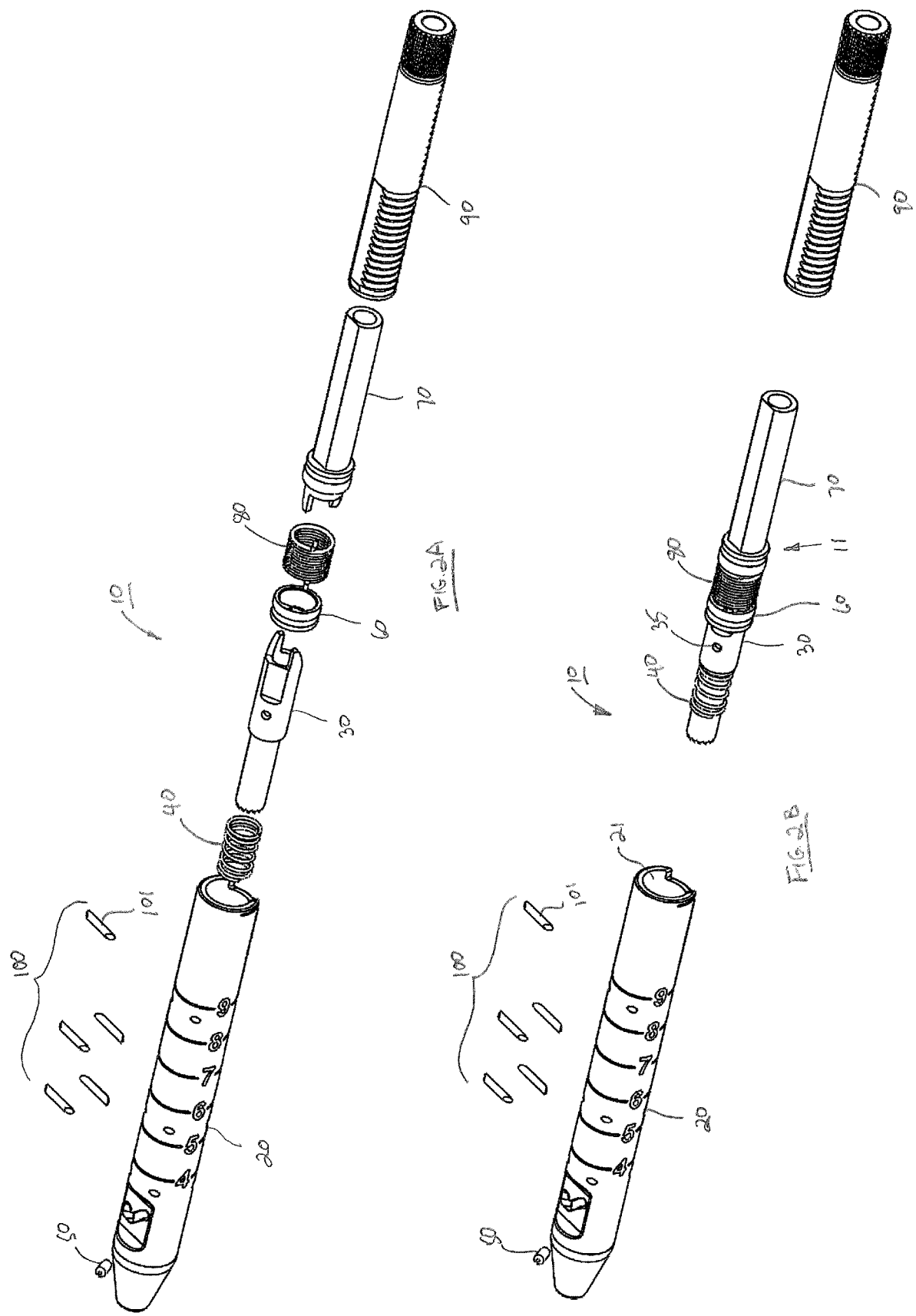

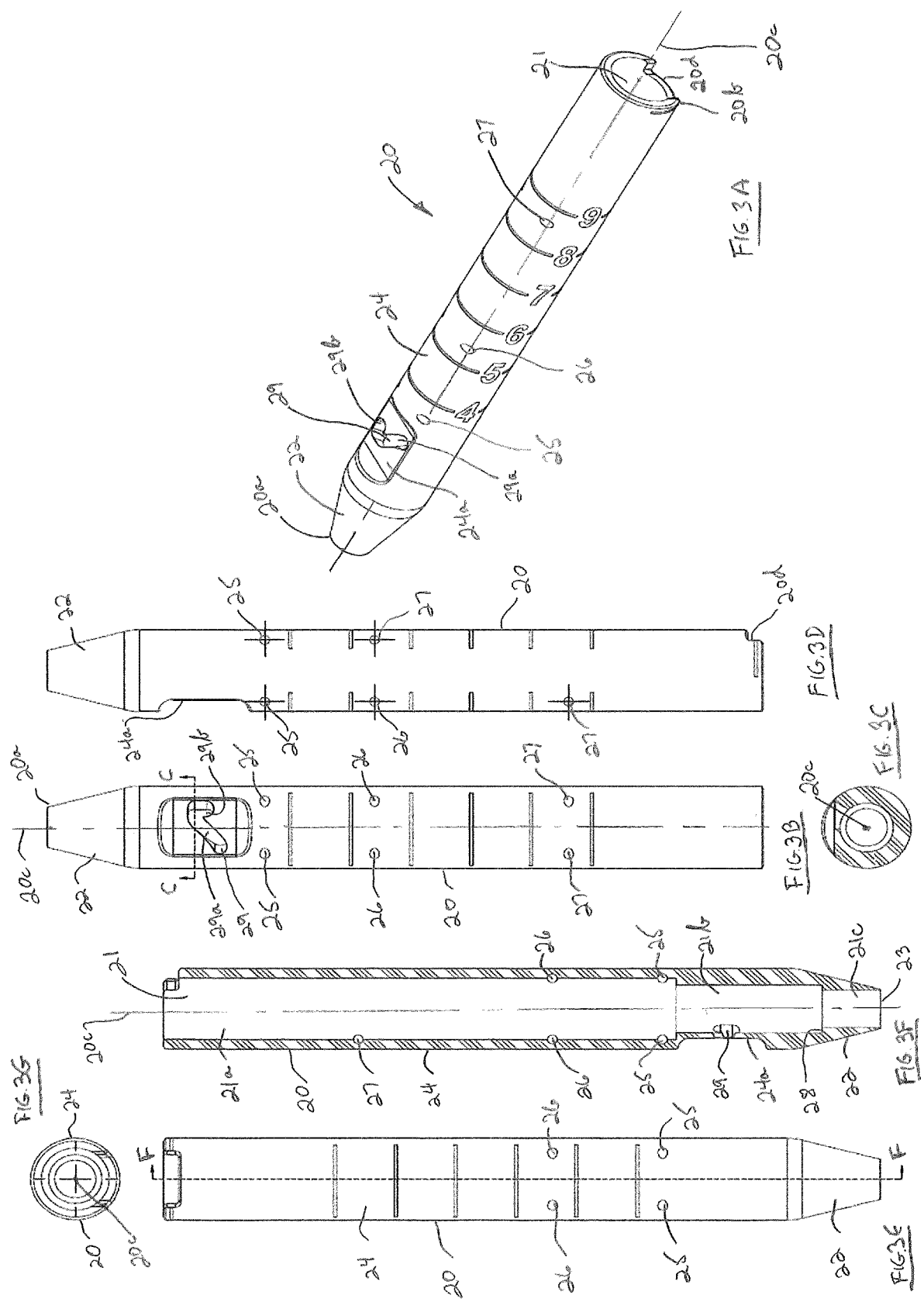

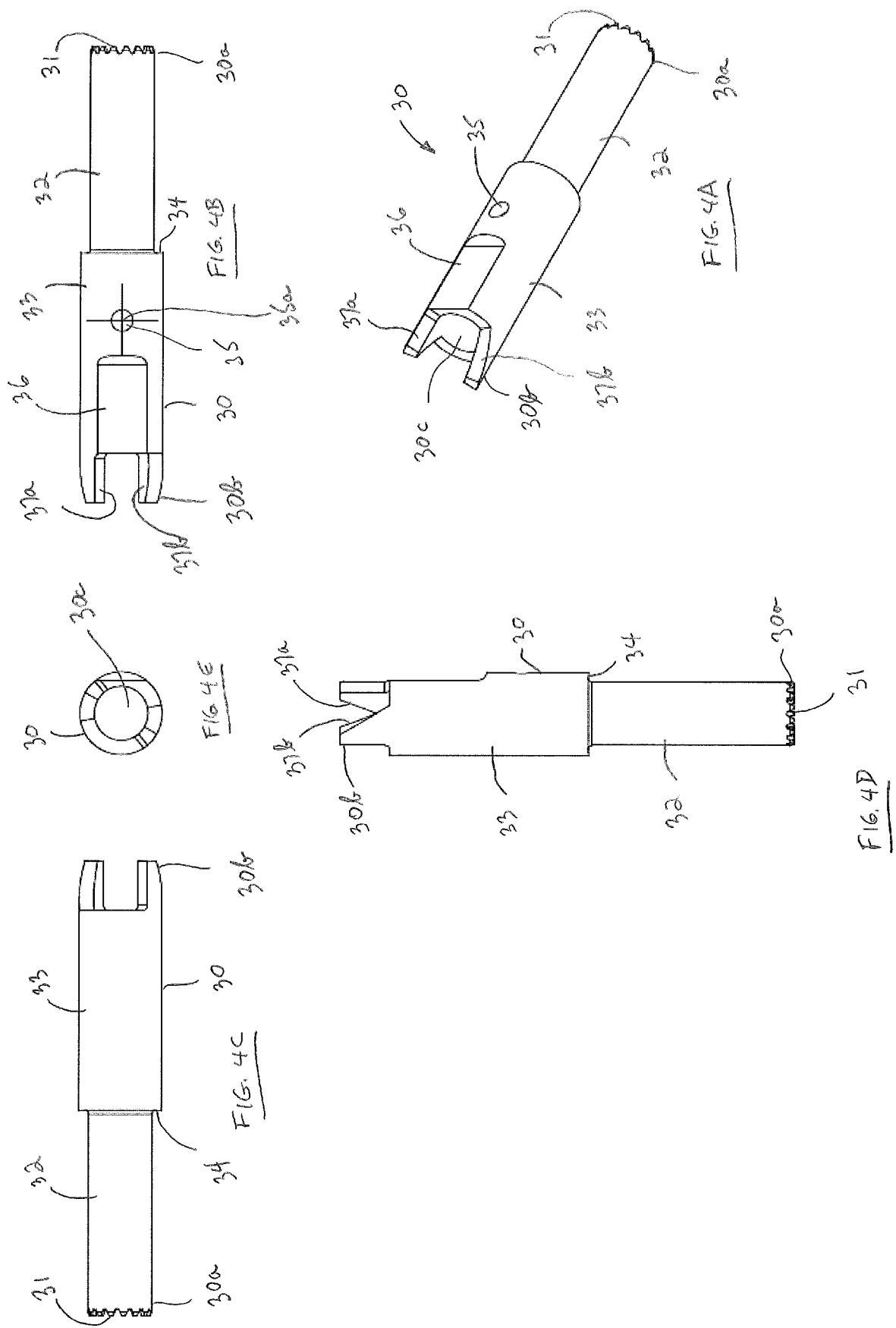

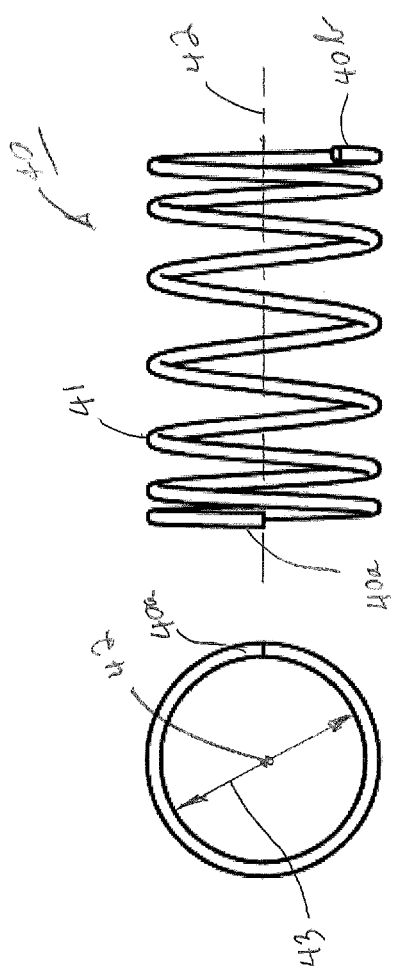
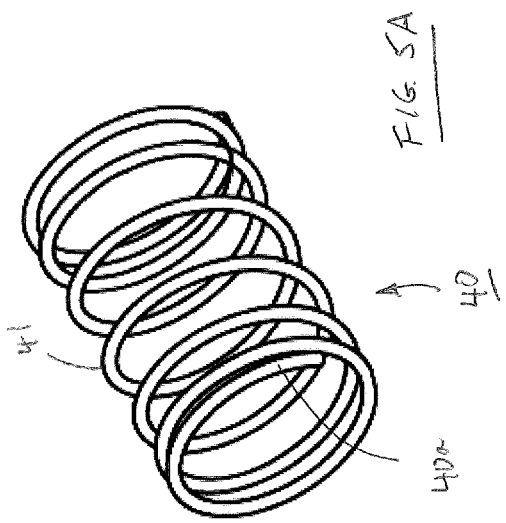

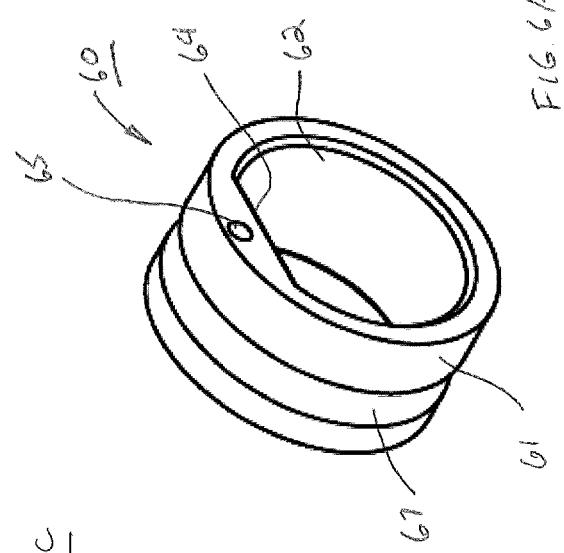
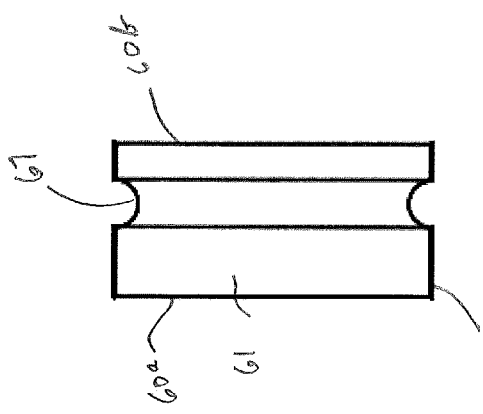
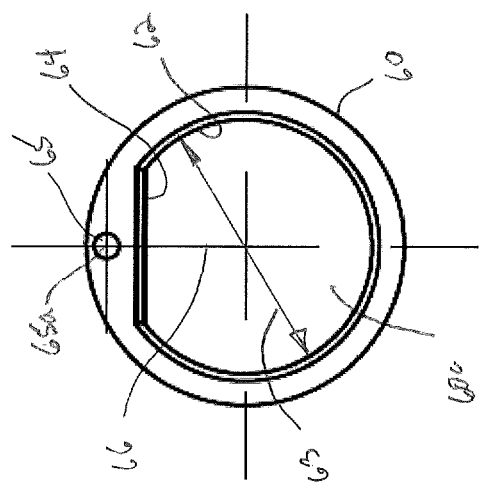
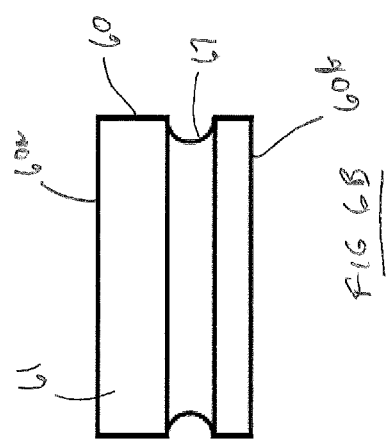

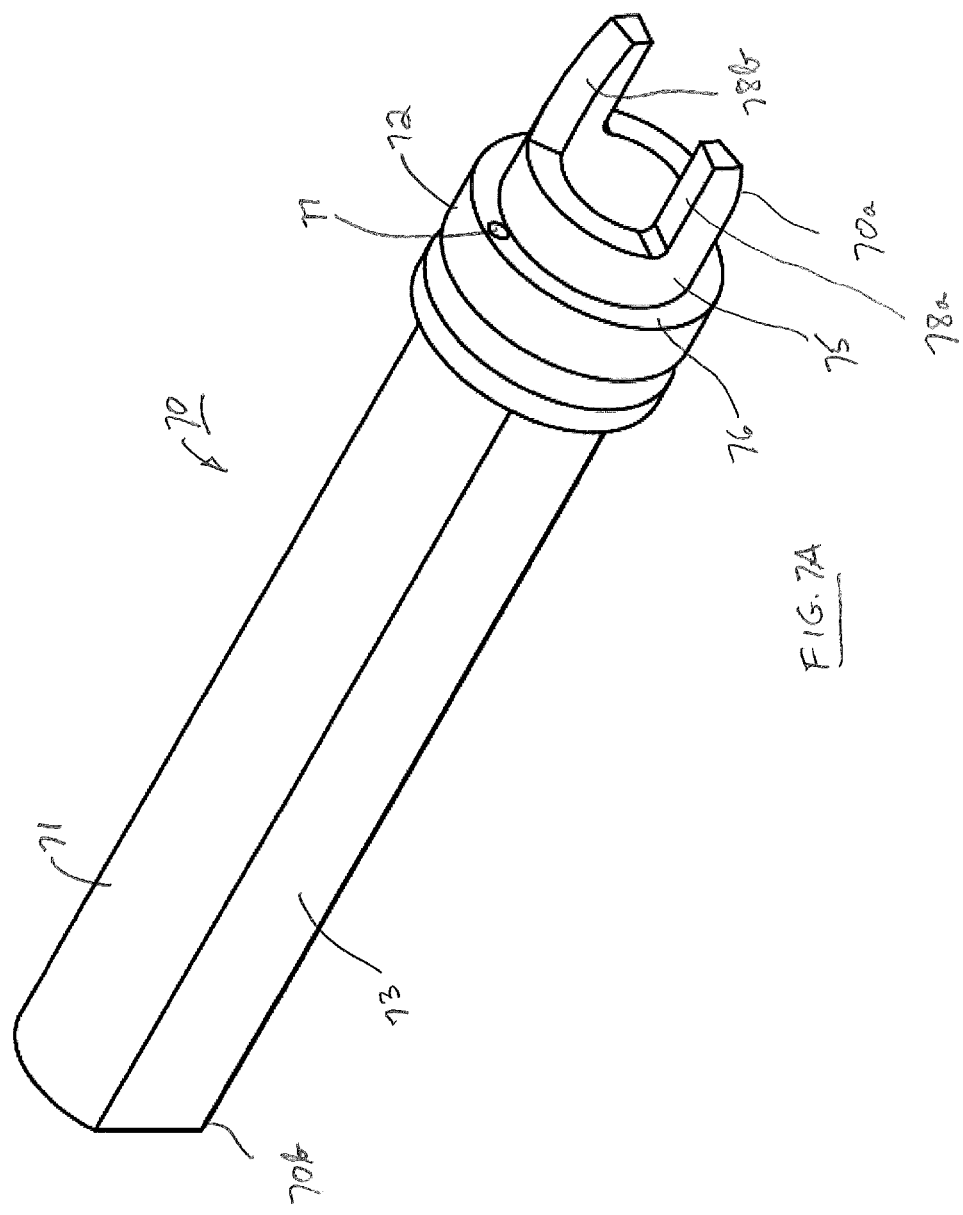
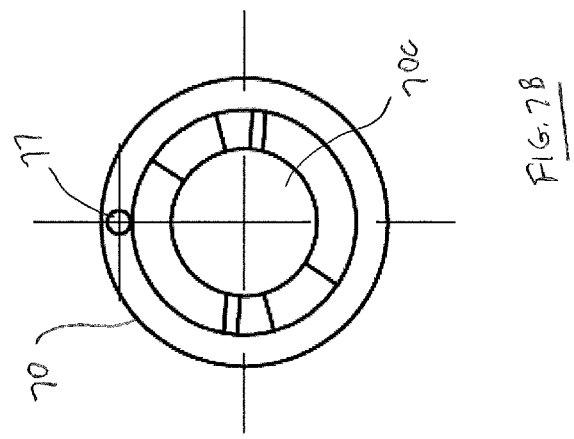
FIG. 7A
FIG. 7B

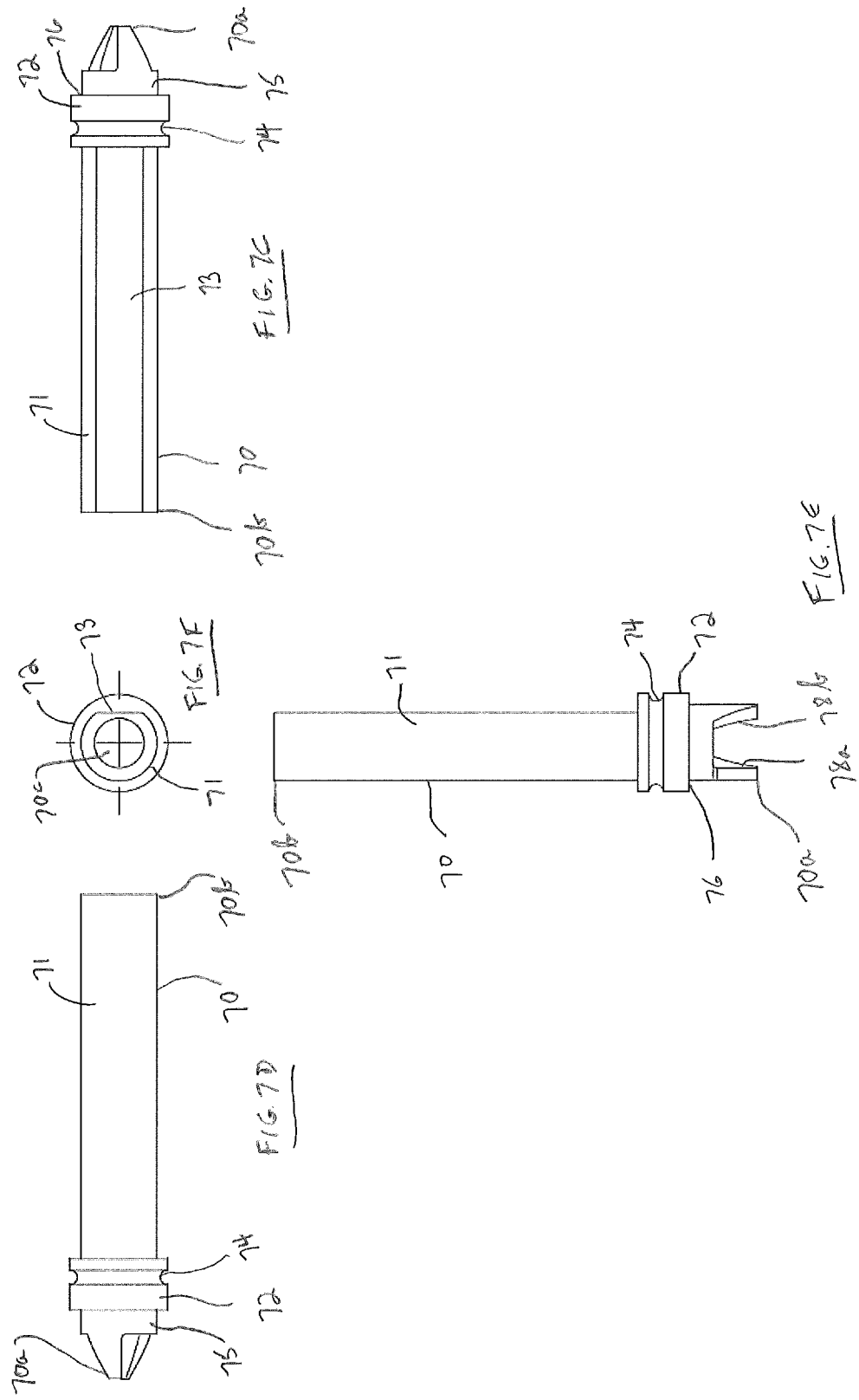

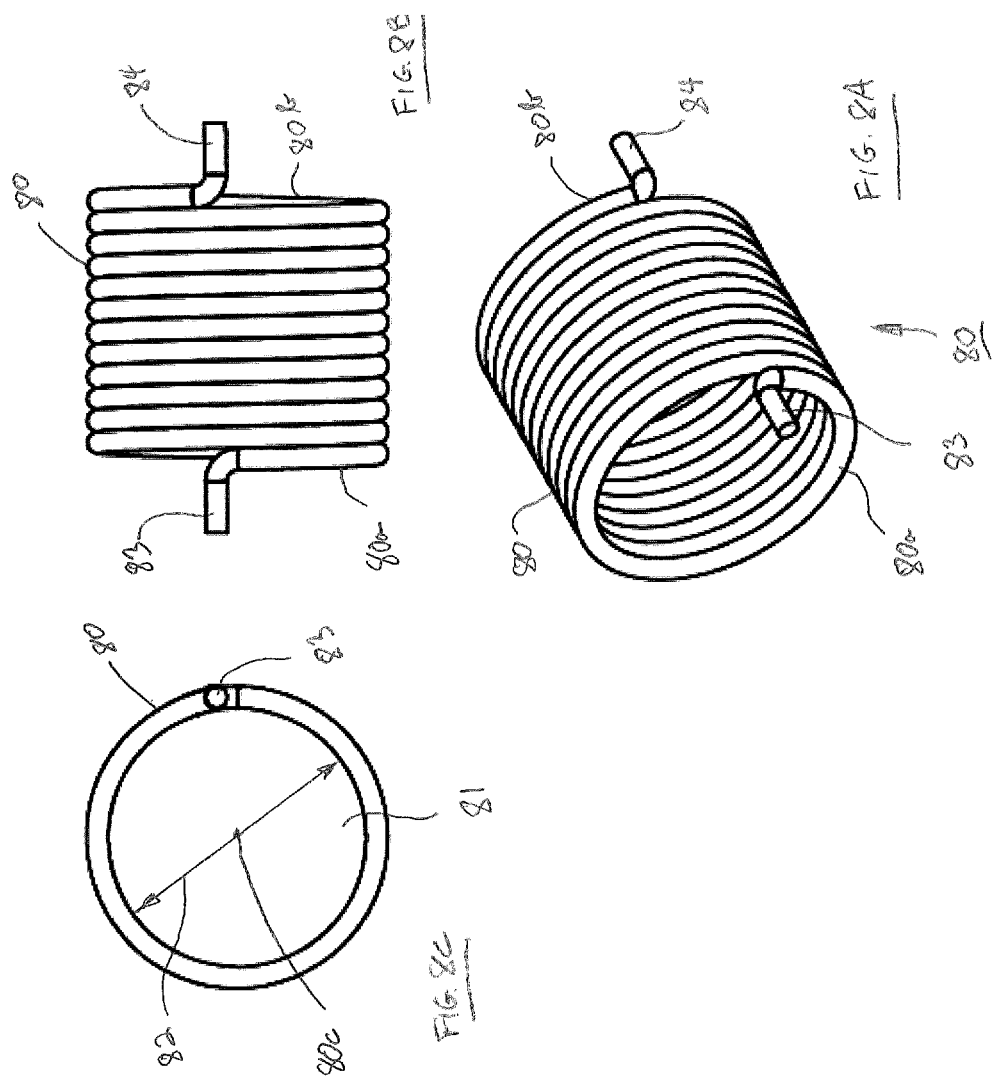

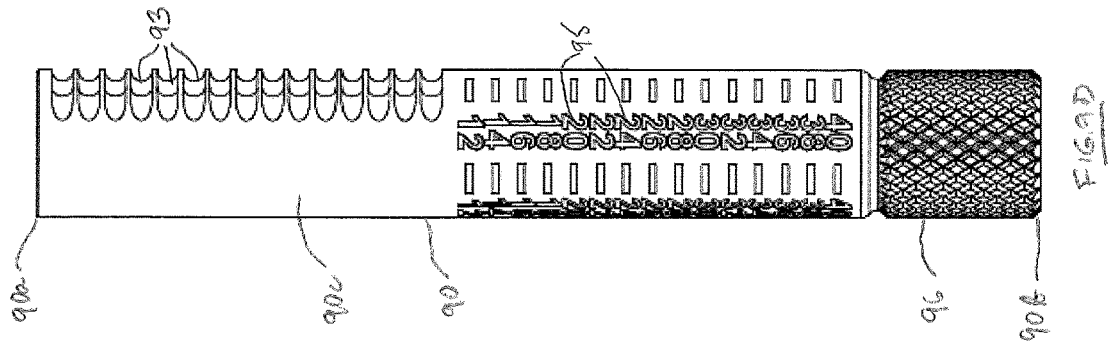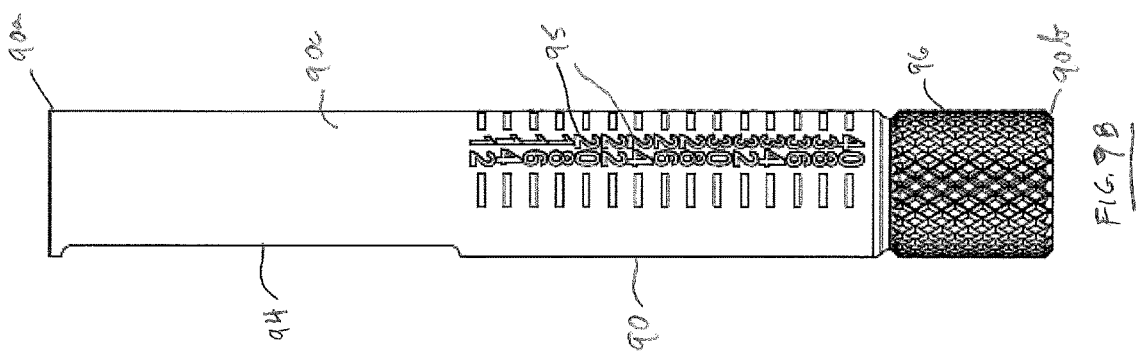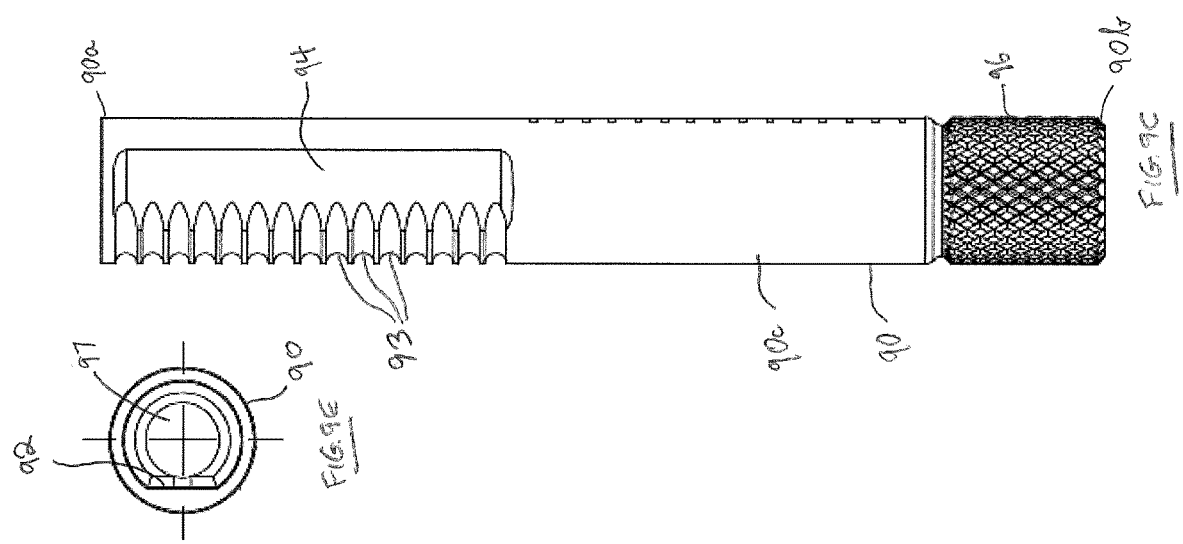

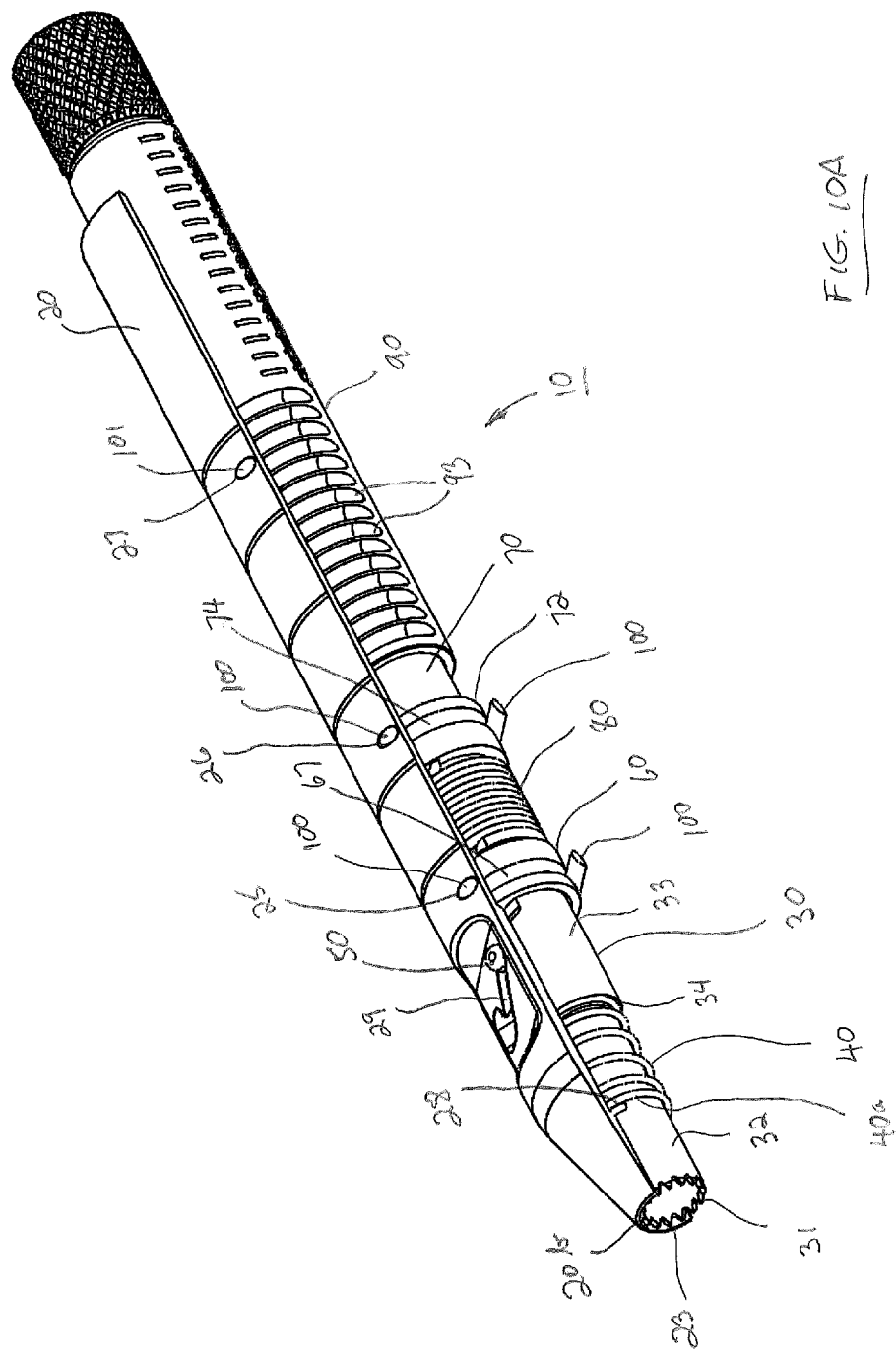

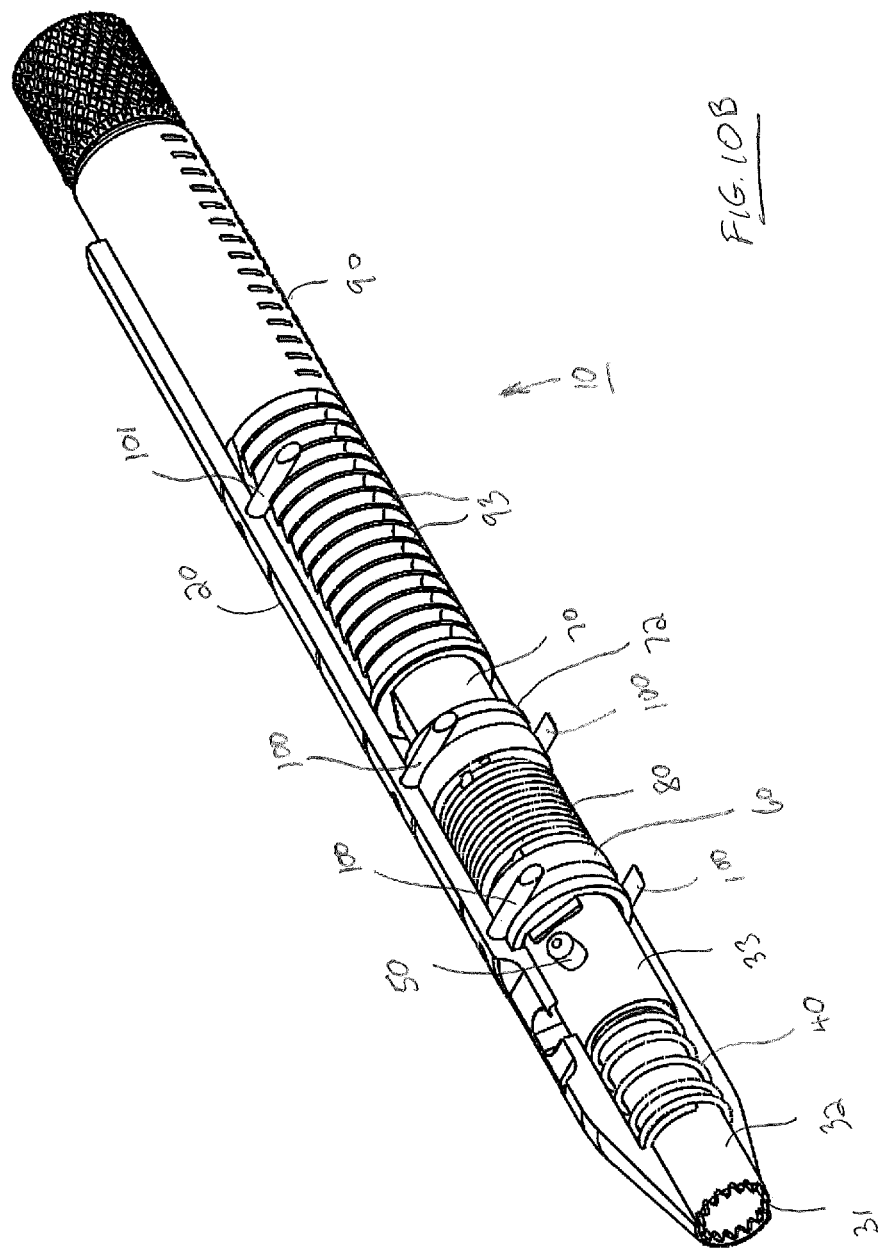

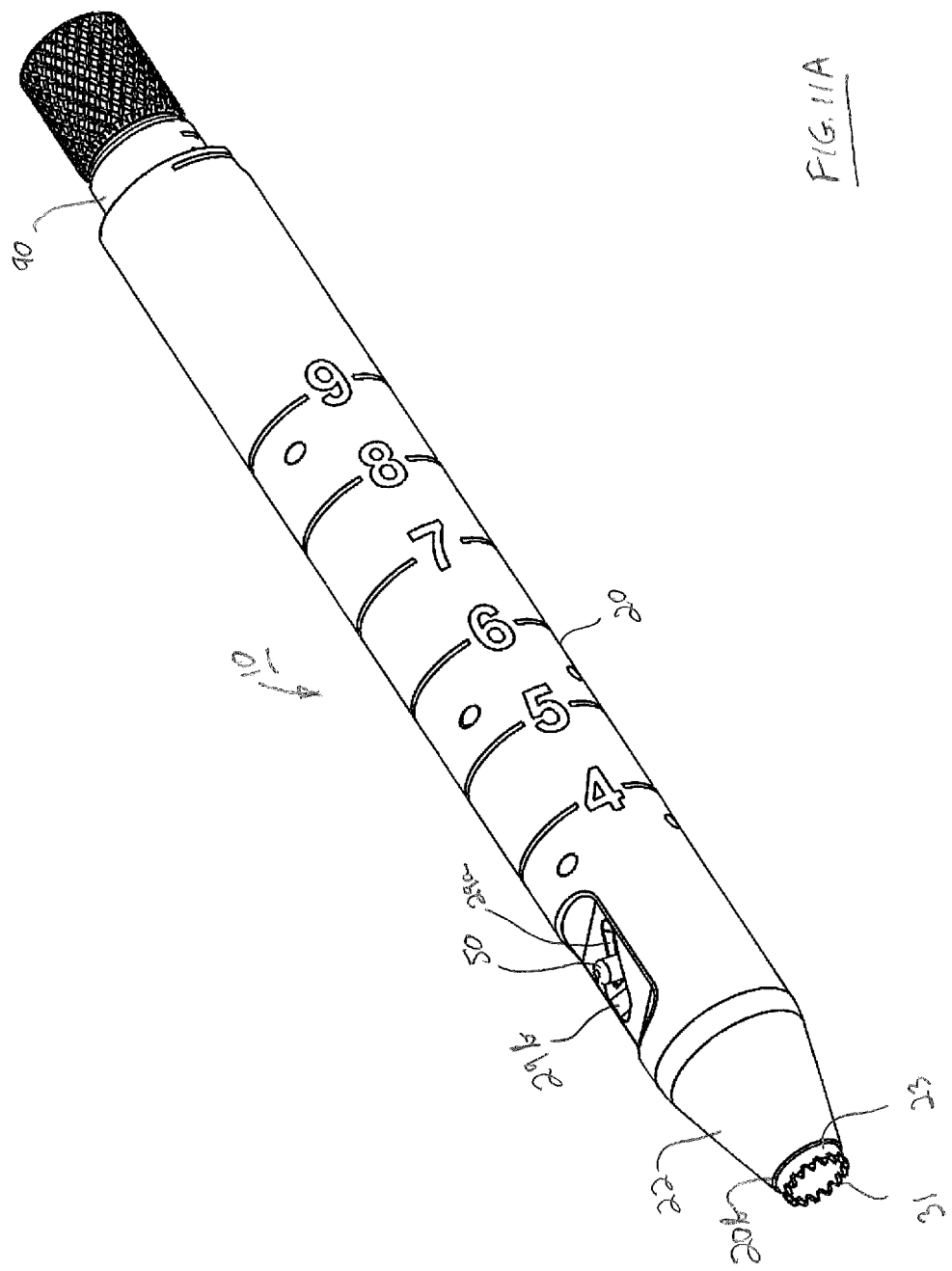

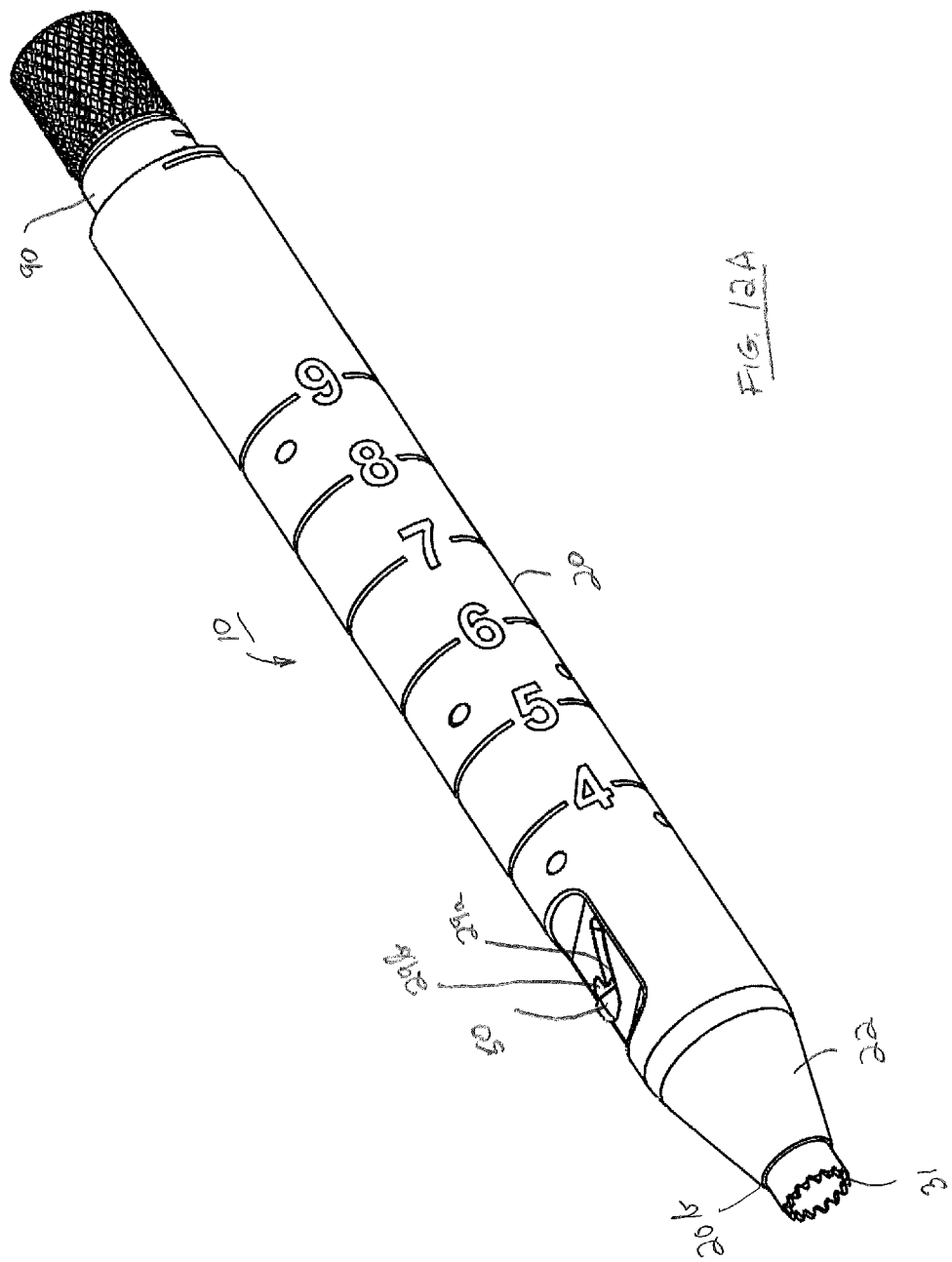

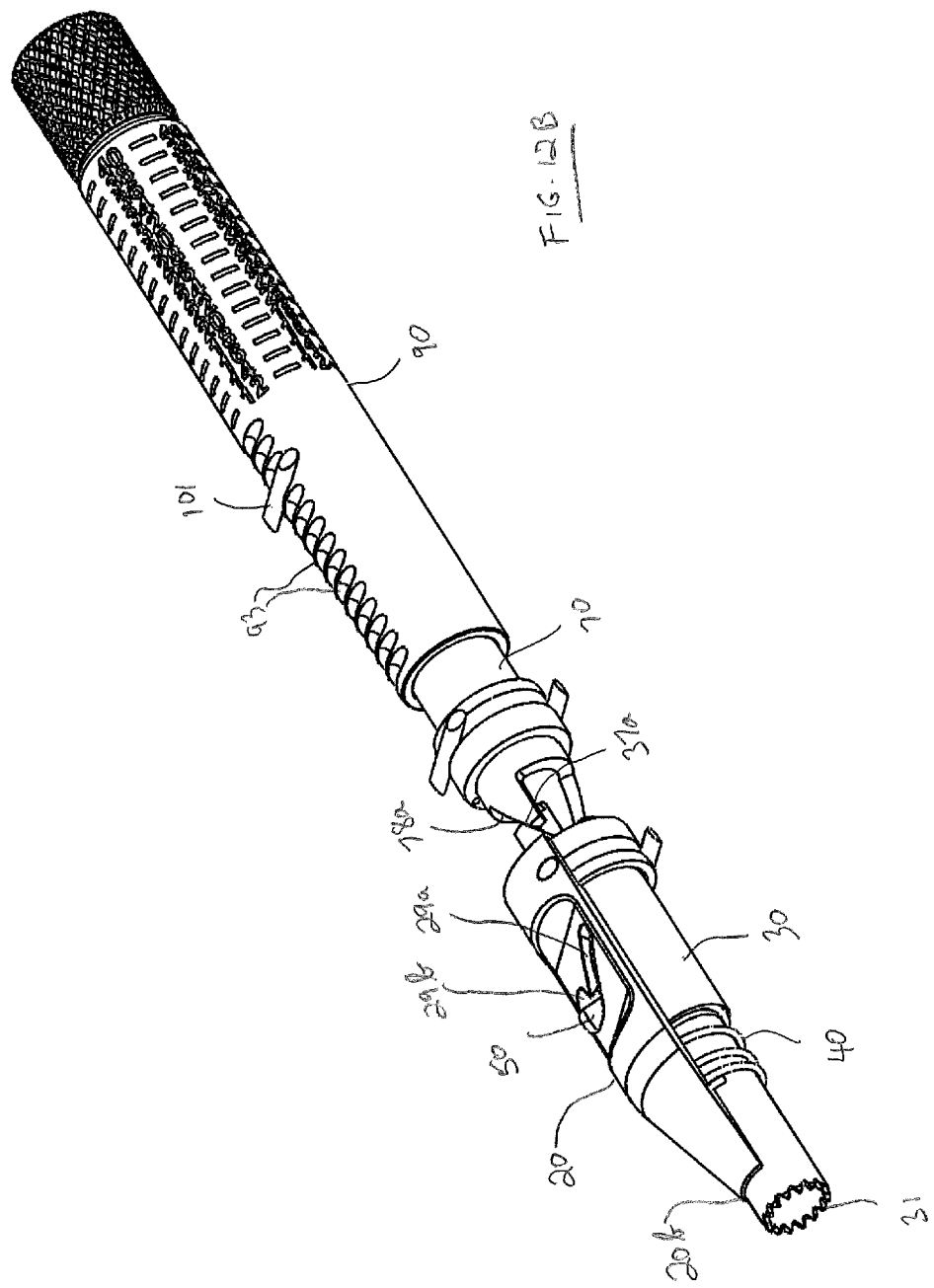

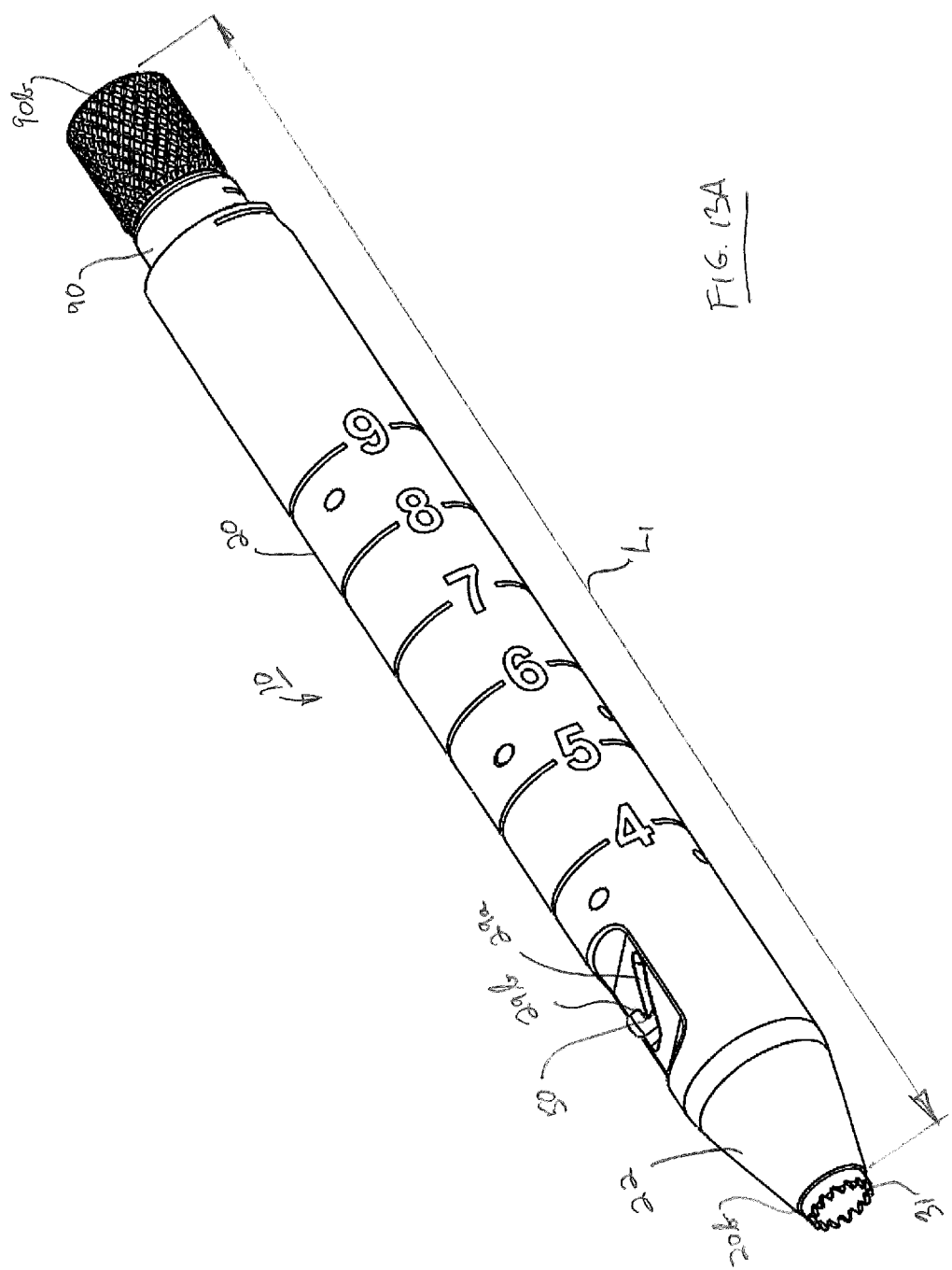

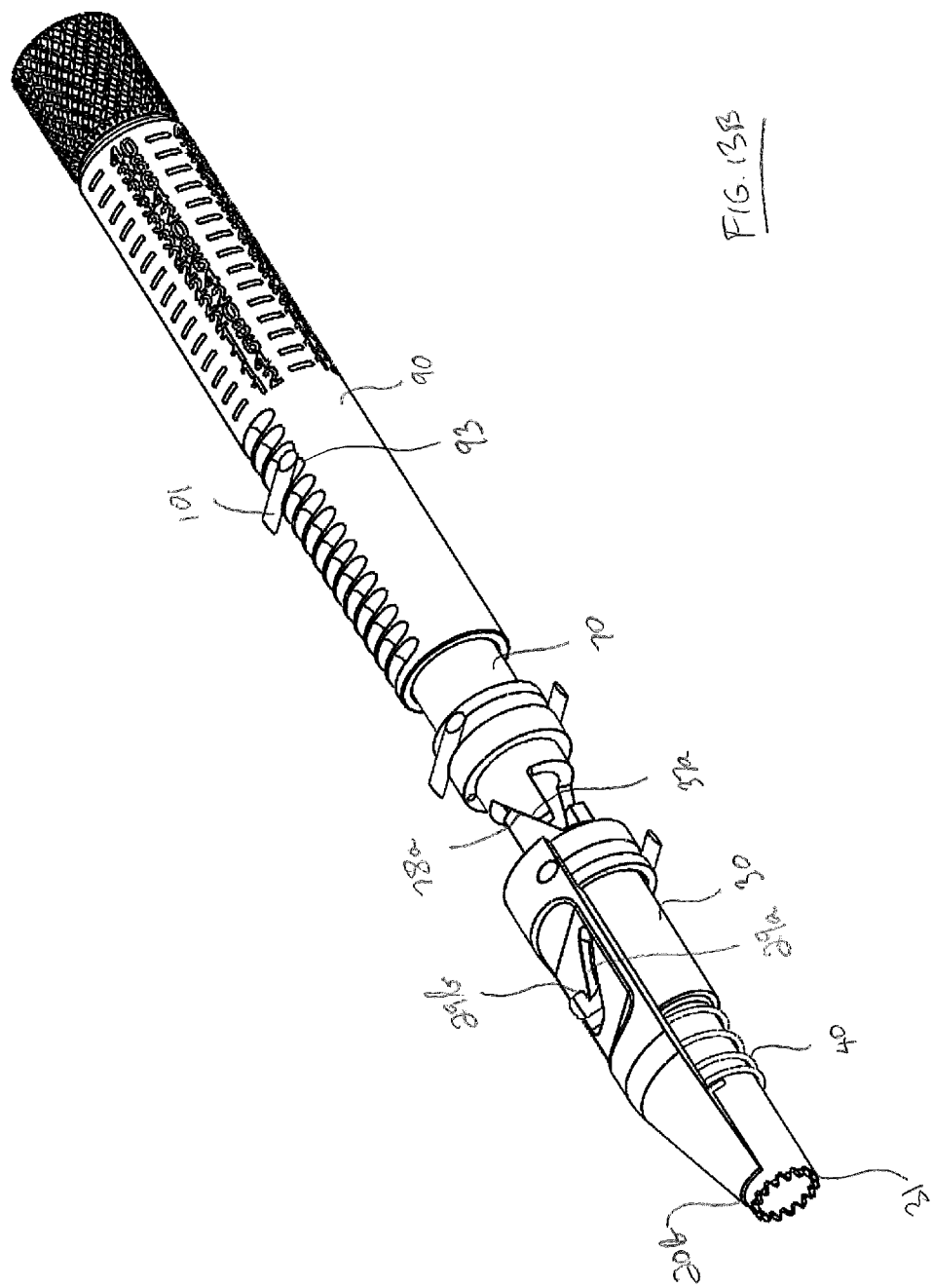

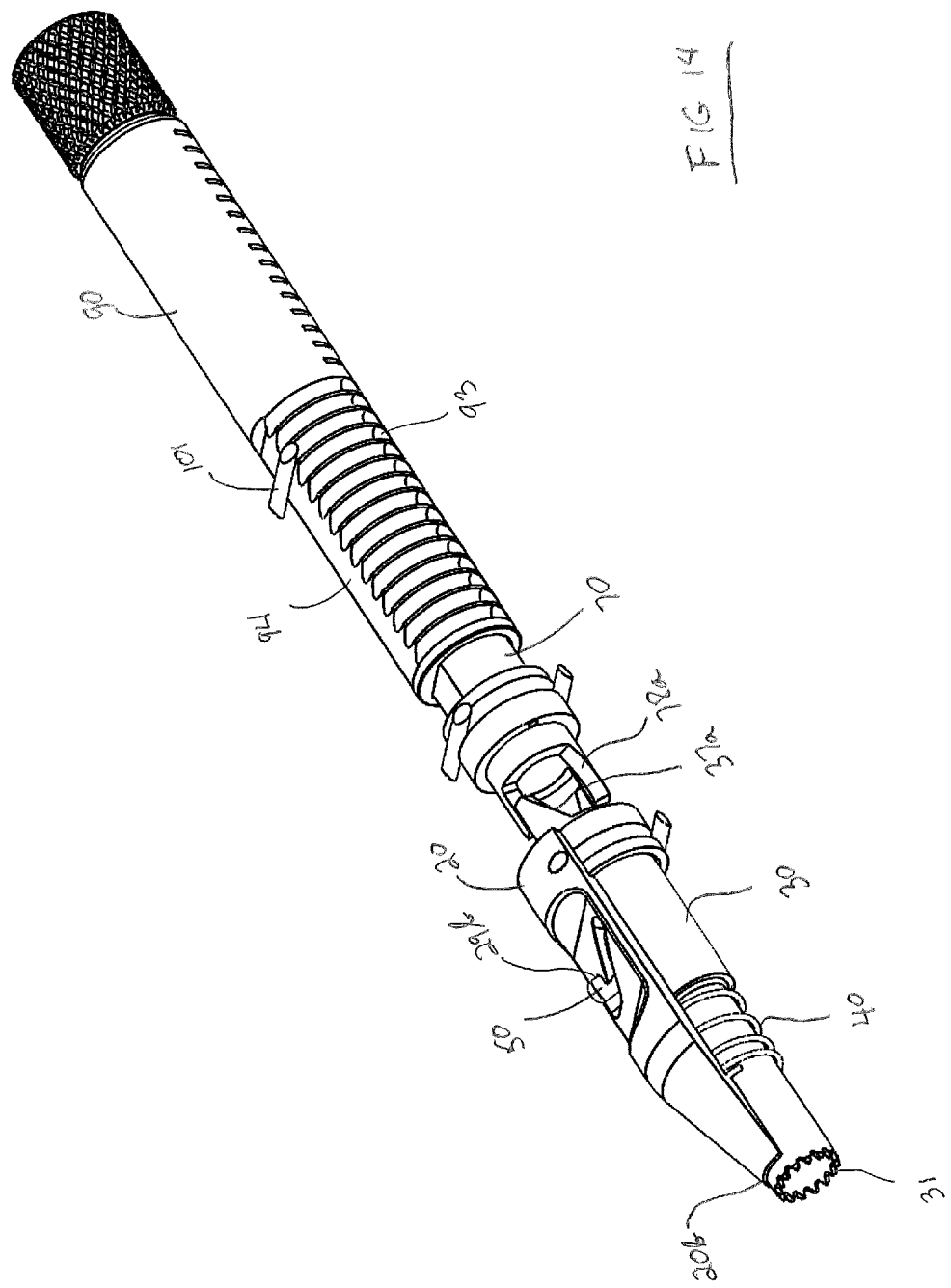

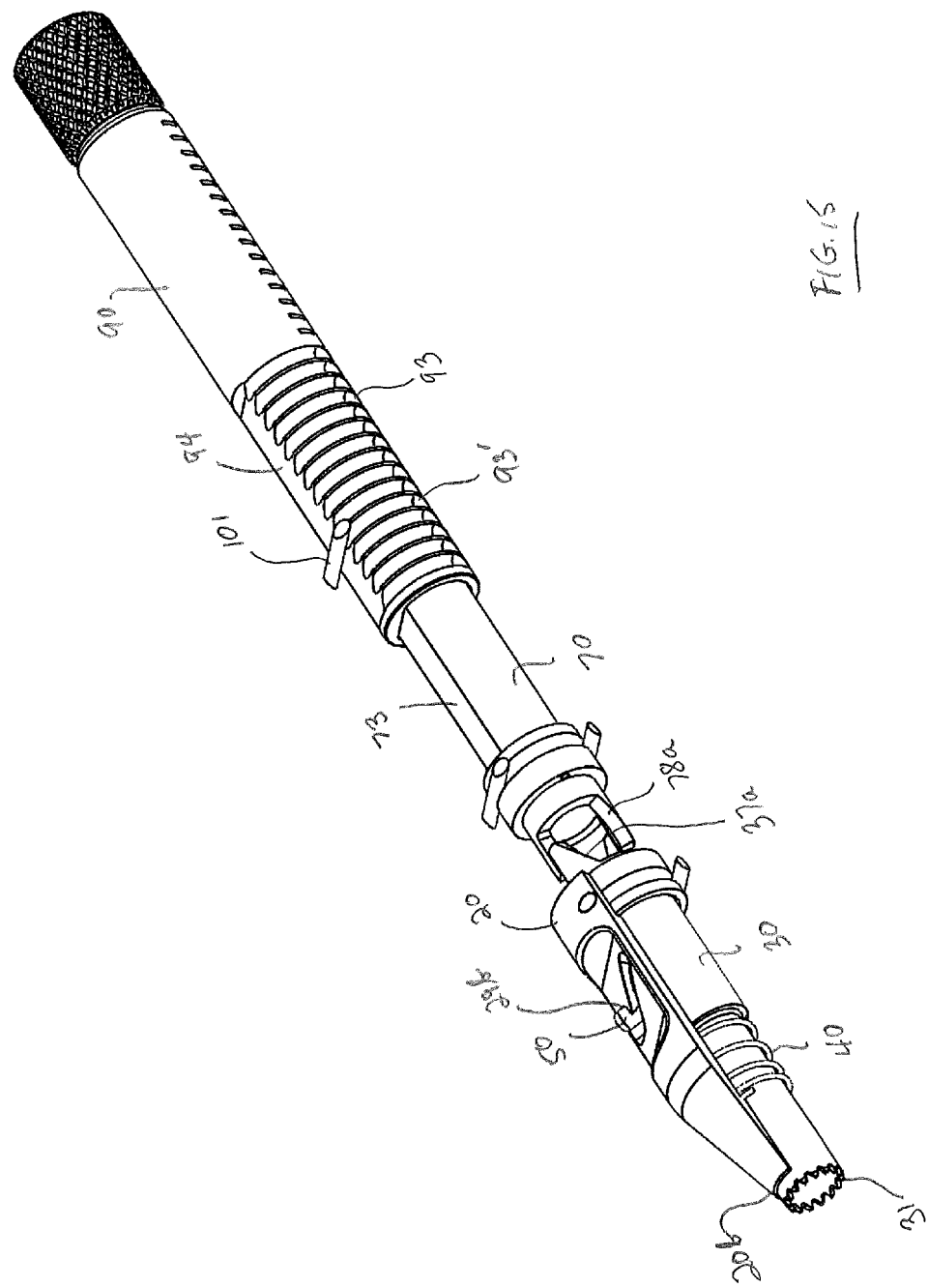

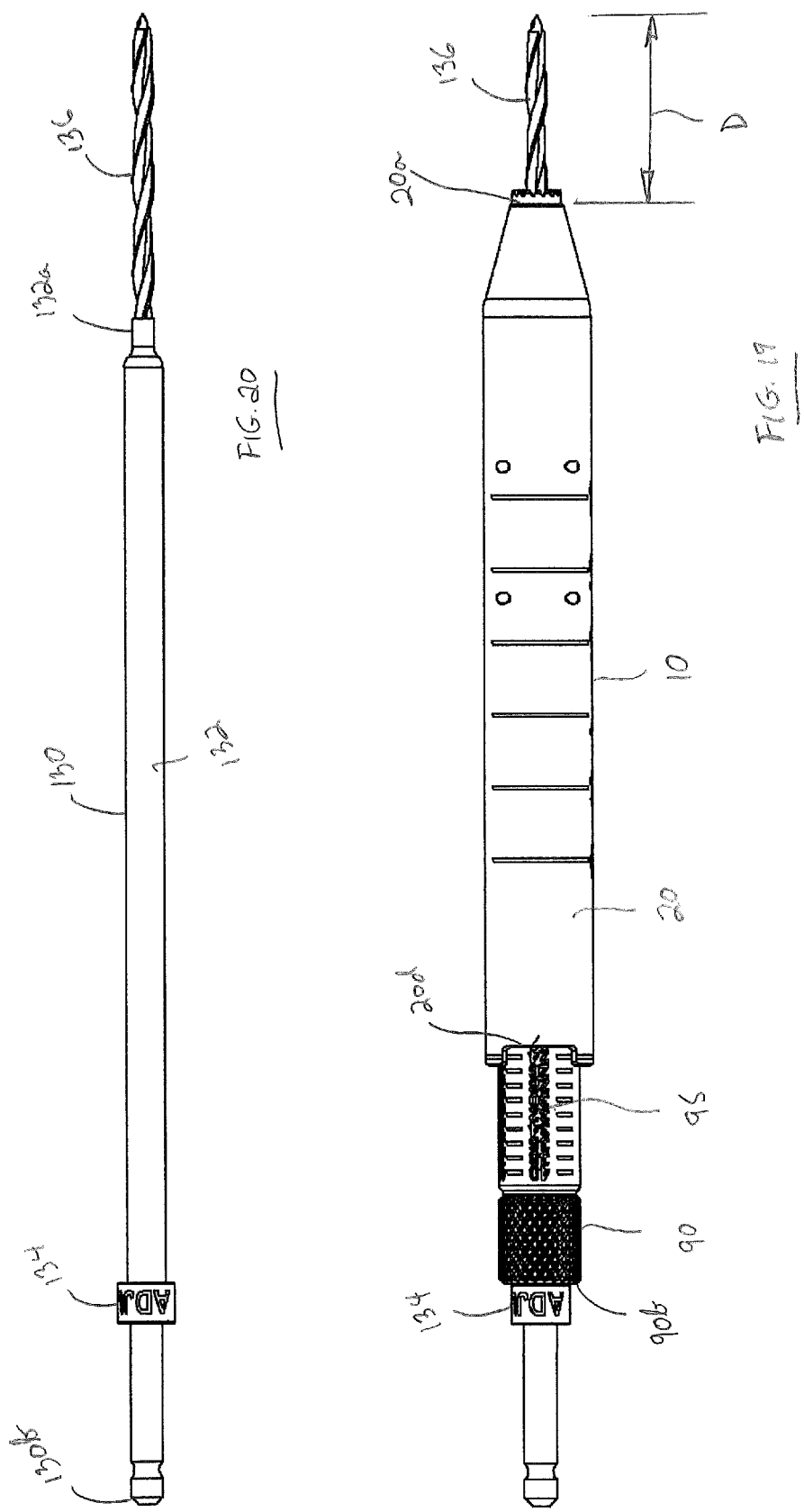

DRILL TAP DILATOR

CROSS-REFERENCE TO RELATED APPLICATION

This application claims the benefit of U.S. Provisional Patent Application No. 62/804,947, filed Feb. 13, 2019, the entire contents of which are incorporated by reference herein.

FIELD OF THE INVENTION

The subject invention relates to an instrument for use in spinal surgery, and more particularly to a dilator for use in facilitating screw placement in cervicothoracic stabilization surgery.

BACKGROUND OF THE INVENTION

In U.S. Patent Publication No. 2019/0342648 entitled "Lateral Mass Fixation Implant", published Dec. 3, 2015, McCormack et al. describe a system and method for providing lateral mass fixation in the cervical spine using a posterior access. The inventors recognize that while anterior cervical spinal fusion is considered less traumatic, they believe that posterior cervical fusion with lateral mass screw or pedicle screw fixation provides a more rigid construct than anterior plates, interbody fusion or interspinous wiring. Nevertheless, the ability to ensure proper placement of fixation devices, especially in less invasive procedures has been found to be more difficult using the posterior access approach. For example, the starting of a pilot hole into the lateral mass and the subsequent tapping, drilling and introduction of a screw into the hole is tedious if the hole position is not maintained throughout the procedure. Certain drill guides for spinal surgery include pointed projections to help stabilize the drill guide against bone structure so as to reduce slippage. Such a drill guide is disclosed, for example, in U.S. Pat. No. 9,119,645, entitled "Pedicle Drill Guide for Spinal Surgery", issued on Sep. 1, 2015 to George Grady McBride. A potential challenge for the McBride drill guide is that the pointed projections are always exposed, and as such, they may impede with surrounding tissue upon entrance into the surgical site. In addition to minimizing or preventing instrument slippage and possible tissue damage, it is also desirable for the drill guide to be adjustable to provide a range of depths that a drill or tap may penetrate into the cervical bone. Certain spinal surgery instruments use separate depth gauges to verify proper bone penetration depth, such as the instruments disclosed in U.S. Pat. No. 6,241,729, entitled "Method and Instrumentation for Posterior Interbody Fusion", issued on Jun. 5, 2001 to Bradley T. Estes et al.

Accordingly, it is desirable to have a dilator that combines dilation, bone docking, and depth stop adjustment in one instrument that would be placed in position throughout the procedure to not only reduce the chance of losing the surgical site but to also save time during surgery.

SUMMARY OF THE INVENTION

It is an object of the invention to provide an improved dilator for posterior spinal fixation.

In accordance with one aspect, the subject drill tap dilator helps to aid in minimally invasive surgical options, particularly in cervicothoracic stabilization surgery. The drill tap instrument is particularly configured to reduce surgical steps, minimize damage to the surgical site tissues while inserting the dilator with a small profile to reduce impedance with the surrounding tissues. The drill tap dilator can be used with both lateral mass screw placement and cervical pedicle screw placement and may be used in both open and mini-open surgical techniques.

In another aspect, the subject drill tap dilator has teeth that are initially disposed in a retracted state. After using the front distal face of the dilator to press through tissue and dilate to the intended surgical site, the teeth can be extended with a control knob on the user end to dock into bone. Docking onto the bone around this intended surgical site often provides a solution, including the maintenance of the location of an already prepared surgical site and the reduction of the risk to the patient caused by drill and tap slippage.

In a further aspect, the subject dilator has an adjustable length with a stop face on the proximal back end of the instrument. Control of the adjustable length is achieved with the control knob on the user end of the instrument. This feature also minimizes or prevents over penetration of drills and taps.

Therefore, a dilator that combines dilation, bone docking, and depth stop adjustment keeps one instrument placed in position throughout the hole preparation procedure thereby reducing the chance of losing the surgical site and the potential of decreasing surgical time.

Other objects and benefits of the invention will become apparent upon consideration of the following written description taken together with the accompanying figures.

DESCRIPTION OF THE FIGURES

FIG. 1 is a perspective view of an exemplary embodiment of a drill tap dilator of the subject invention with docking teeth being in a retracted position.

FIG. 2A is an exploded perspective view of the drill tap dilator of FIG. 1.

FIG. 2B is an exploded perspective view of the drill tap dilator of FIG. 2A with certain internal components being shown in a subassembly.

FIG. 3A is a top perspective view of the elongate dilator body of FIG. 2A.

FIG. 3B is a top plan view of the elongate dilator body of FIG. 3A.

FIG. 3C is a cross-sectional view of the elongate dilator body as seen along viewing lines C-C of FIG. 3B.

FIG. 3D is a side elevation view of the elongate dilator body of FIG. 3A.

FIG. 3E is a bottom plan view of the elongate dilator body of FIG. 3A.

FIG. 3F is a cross-sectional view of the elongate dilator body as seen along viewing lines F-F of FIG. 3E FIG. 3G is an end view the elongate dilator body of FIG. 3E.

FIG. 4A is a is a top perspective view of the elongate sleeve of FIG. 2A.

FIGS. 4B and 4C are respective top and bottom plan views of the elongate sleeve of FIG. 4A.

FIG. 4D is a side elevation view of the elongate sleeve of FIG. 4A.

FIG. 4E is a distal end view the elongate dilator body of FIG. 4A.

FIGS. 5A, 5B and 5C illustrate respectively, perspective, side and end views of the compression spring of FIG. 2A.

FIG. 6A is a top perspective view of the keying ring of FIG. 2A

FIGS. 6B, 6C and 6D illustrate respectively, bottom, side and end views of the keying ring of FIG. 6A.

FIG. 7A is a top perspective view of the drive shaft of FIG. 2A

FIG. 7B is an end view of the distal end of the drive shaft of FIG. 7A.

FIGS. 7C and 7D are respectively, right side and left side elevation views of the drill shaft of FIG. 7A.

FIG. 7E is a bottom plan view of the drill shaft of FIG. 7A.

FIG. 7F is an end view of the proximal end of the drive shaft of FIG. 7A.

FIGS. 8A, 8B and 8C illustrate respectively, perspective, side and end views of the compression spring of torsion spring of FIG. 2A.

FIGS. 9B, 9C and 9D are respectively, top plan, right side and left side elevation views of the control knob of FIG. 9A.

FIG. 9E is an end view of the distal end of the control knob of FIG. 9C.

FIGS. 10A, 10B and 10C are perspective views showing different cutaway portions of the elongate dilator body to reveal details of the assembled internal components of drill tap dilator in the same position as shown in FIG. 1.

FIG. 11A is the view of the drill tap dilator of FIG. 10A showing docking teeth and a guide pin in an intermediate location wherein docking teeth start to project distally from the distal end of drill tap dilator.

FIG. 12A is a perspective view of the drill tap dilator showing docking teeth fully axially projected and the corresponding location of the guide pin in a slot formed in drill tap dilator.

FIG. 12B is the view of the drill tap dilator of FIG. 12A showing a cutaway portion to reveal details of internal components in the fully projected position of docking teeth.

FIG. 13A is the view of the drill tap dilator showing docking teeth slightly axially retracted and the corresponding location of the guide pin in a hooked slot for locking the position of docking teeth.

FIG. 13B is the view of drill tap dilator of FIG. 13A showing a cutaway portion to reveal details of internal components with the docking teeth in a locked position.

FIG. 14 is the cutaway view of the drill tap dilator of FIG. 13B with the docking teeth in a locked position and with the control knob rotated counterclockwise to a position to allow adjustment of the length of the drill tap dilator.

FIG. 15 is the view of drill tap dilator FIG. 14 showing an increase in the length of the drill tap dilator by axial movement of the control knob.

FIG. 19 is a side elevation view of the drill tap dilator of the subject invention in use with a drill.

FIG. 20 is a side elevation view of the drill of FIG. 19.

DESCRIPTION OF THE EMBODIMENTS

Figure 9A:
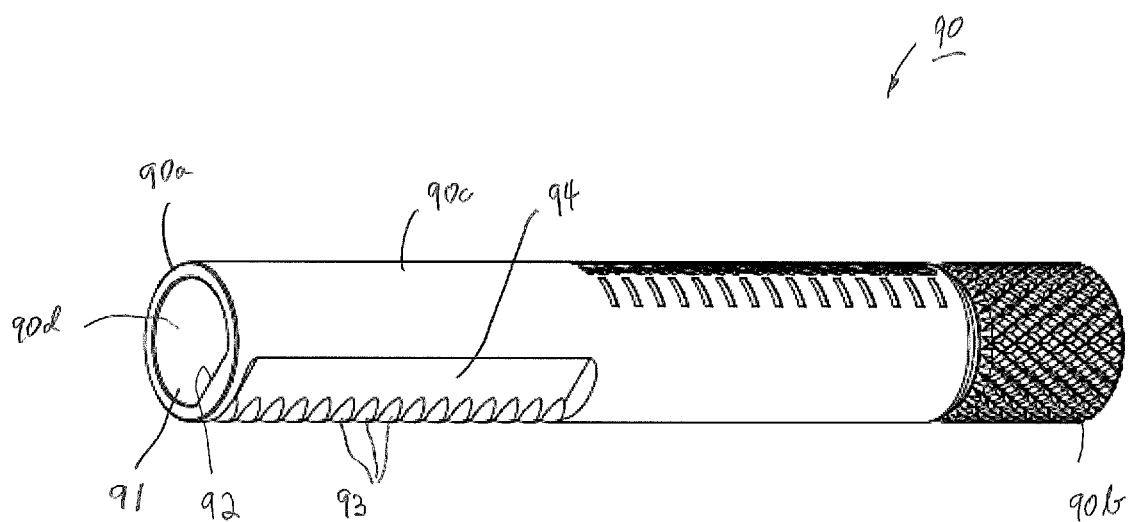
FIG. 9A is a side perspective view of the control knob of FIG. 2A.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Turning now to FIG. 1 a drill tap dilator 10 in accordance with an exemplary embodiment is shown. Drill tap dilator 10 helps to aid in the minimally invasive placement of screws for spinal fixation particularly, but not exclusively, in cervicothoracic stabilization surgery. Drill tap dilator 10 may be used with both lateral mass screw placement and cervical pedicle screw placement in either open or mini-open surgical techniques. As will be described, drill tap dilator 10 may be adapted for use with a tap or drill in preparation for the threadable introduction of a lateral mass screw or pedicle screw that may then be used for rigid connection to a suitable fixation rod to stabilize the cervicothoracic spinal segment.

Turning now to FIGS. 2A and 2B, components of drill tap dilator 10 are now described. The exemplary drill tap dilator 10 comprises the following elements: an elongate dilator body 20, an elongate sleeve 30, a biasing element 40, a guide pin 50, a keyed ring 60, an elongate drive shaft 70, a torsion spring 80, an elongate control knob 90 and a series of support pins 100. One support pin 100 serves as control pin 101. These components are described as follows.

Details of the elongate dilator body 20 are shown in FIGS. 3A through 3G. Elongate dilator body 20 has a distal end 20a, a proximal end and 20b and a central lumen 21 extending therethrough along a longitudinal axis 20c. Elongate dilator body 20 comprises a tapered surface 22 extending from distal end 20a and tapering outwardly to an outer cylindrical surface 24. Outer cylindrical surface 24 has an outer diameter that is sized to mate with an outer rigid arm dilator, as will be described. Elongate dilator body 20 has two pair of distally located holes 25 formed therethrough, two pair of centrally located holes 26 and one pair of proximally located holes 27. Holes 25, 26 and 27 each extend transversely through elongate dilator body relative to the longitudinal axis 20c and are sized and configured to receive their respective support pin 100, as will be described. An undercut 20d is provided on proximal and 20b to provide a depth indication window in conjunction with depth markings on control knob 90, as will be described.

Lumen 21 has three portions over the length of elongate dilator body 20, namely first portion 21a, second portion 21b and third portion 21c. The diameter of first portion 21a is larger than the diameter of second portion 21b which is larger than the diameter of third portion 21c. Third portion 21c opens at the distal end 20a of elongate dilator body 20 in a circular exit opening 23 through which docking teeth are configured to project, as will be described. The interface between second portion 21b and third portion 21c defines a shoulder 28 extending transversely within lumen 21 relative to longitudinal axis 20c. Shoulder 28 defines a contact surface for capturing a distal end of biasing element 40, as will be described. An outer flat surface 24a is formed into outer cylindrical surface 24 adjacent distal end 20a in partial alignment with and second portion 21b. A slot 29 is formed through outer flat surface 24a and into lumen second portion 21b. Slot 29 is configured to slidably receive guide pin 50, as will be described. Slot 29 has a first extent 29a and a second extent 29b. Slot first extent 29a extends at an angle relative to longitudinal axis 20c. Slot second extent 29b is formed at the distalmost end of slot first extent 29a and extends proximally along longitudinal axis 20c for a distance to define a hooked opening, as illustrated in FIGS. 3A and 3B.

Turning now to FIGS. 4A through 4E, details of elongate sleeve 30 are now described. Elongate sleeve 30 is configured for slidable receipt within central lumen 21 of elongate dilator body 20 and has a distal end 30a, a proximal end 30b and a lumen 30c extending therethrough. A plurality of docking teeth 31, each being defined by the pointed projection, are formed at distal end 30a of elongate sleeve 30 with docking teeth 31 projecting axially. Elongate sleeve 30 comprises a first distal cylindrical portion 32 and a second proximal cylindrical portion 33, first distal cylindrical portion 32 having a diameter less than the diameter of second proximal cylindrical portion 33. First distal cylindrical portion 32 is sized and configured for slidable receipt within lumen second portion 21b of elongate dilator body 20 and second proximal cylindrical portion 33 is sized and configured for slidable receipt within lumen first portion 21a of elongate dilator body 20. An exterior transverse surface 34 extends radially between first distal cylindrical portion 32 and second proximal cylindrical portion 33, exterior transverse surface 34 defining a contact surface for capturing a proximal end of biasing element 40, as will be described. Second proximal cylindrical portion 33 has an opening 35 having a central axis 35a, opening 35 being configured for receipt and support of guide pin 50. Second proximal cylindrical portion 33 further includes a flat surface 36 formed adjacent proximal end 30b, as shown in FIGS. 4A and 4B. In a particular arrangement, central axis 35a of opening 35 lies orthogonal relative to flat surface 36. Elongate sleeve comprises a pair of opposed inclined force transmission surfaces 37a and 37b that are configured to cooperate with cooperative features on drive shaft 70 to axially move elongate sleeve 30 within central lumen 21 of elongate dilator body 20, as will be described.

Referring now to FIGS. 5A through 5C, details of biasing element 40 are described. In a particular arrangement, biasing element 40 is a compression spring. It should be appreciated, however, that biasing element 40 may also include other elements, such as elastically deformable materials. Compression spring 40 is conventionally formed by a helically wound metallic wire 41 in a cylindrical configuration defined by a longitudinal axis 42. As so formed, compression spring 40 has a distal and 40a and a proximal and 40b. Compression spring 40 has an inner diameter 43 configured to receive first distal cylindrical portion 32 of elongate sleeve 30. Distal end 40a is configured to engage transversely extending shoulder 28 within central lumen 21 of elongate dilator body 40. Proximal end 40b is configured to engage exterior transverse surface 34 extending radially between first distal cylindrical portion 32 and second proximal cylindrical portion 33. Application of opposite axial forces along longitudinal axis 42 will cause compression spring 40 to axially compress with compression spring 40 inherently producing an opposite axial compression force.

Turning now to FIGS. 6A through 6D, details of keying ring 60 are described. Keying ring 60 has a distal end 60a, a proximal end 60b and a central opening 60c extending therethrough. Keying ring 60 has an outer cylindrical surface 61 and an inner cylindrical surface 62. Central opening 60c is defined by inner cylindrical surface 62 and has a diameter 63 that is sized and configured to sliding receive second proximal cylindrical portion 33 of elongate sleeve 30. Central opening 60c is truncated by an internal flat surface 64 lying as a chord within diameter 63 of central opening 60c. Proximal end 60b includes a hole 65 formed therein for receipt of a portion of torsion spring 80, as will be described. Hole 65 lies with its center axis 65a on a radial line 66 that is orthogonal to internal flat surface 64, as depicted in FIG. 6D. When keying ring 60 is inserted on second proximal cylindrical portion 33 of elongate sleeve 30, internal flat surface 64 will contact flat surface 36 of elongate sleeve 30 thereby positioning keying ring 60 in a keyed disposition relative to elongate sleeve 30. In such keyed disposition, rotational movement between elongate sleeve 30 and keying ring 64 is prevented while relative axial movement therebetween is allowed. Keying ring 60 further includes an arcuate recess 67 extending within outer cylindrical surface 61 as shown in FIGS. 6B and 6C. As will be described, recess 67 is configured to receive a pair of support pins 100 extending thereacross in a manner to axially hold the position of keying ring 60 relative to elongate dilator body 20 while allowing relative rotation between keying ring 60 and elongate dilator body 20.

Referring now to FIGS. 7A through 7E, details of drive shaft 74 are now described. Drive shaft 70 is elongate having a distal end 70a, a proximal end 70b and a lumen 70c extending therethrough. Drive shaft 70 provides a mechanism for transmitting torque, as will be described, from control knob 90 to elongate sleeve 30 and hence docking teeth 31 and then back under the influence of torsion spring 80 from keying ring 62 to control knob 90. Drive shaft 70 comprises a first proximal cylindrical portion 71 and a second distal cylindrical portion 72, first proximal cylindrical portion 71 having a diameter less than the diameter of second distal cylindrical portion 72. First proximal cylindrical portion 71 is sized and configured for slidable receipt within a lumen of control knob 90, as will be described. First proximal cylindrical portion 71 further includes an exterior flat surface 73 formed substantially from proximal end 70b of first proximal cylindrical portion 71 to second cylindrical portion 72, as shown in FIGS. 7A and 7C. Second distal cylindrical portion 72 is sized and configured for slidable receipt within lumen first portion 21a of elongate dilator body 20. Drive shaft 70 further includes an arcuate recess 74 extending within second distal cylindrical portion 72, as shown in FIGS. 7C, 7D and 7E. As will be described, recess 74 is configured to receive a pair of support pins 100 extending thereacross in a manner to axially hold the position of drive shaft 70 relative to elongate dilator body 20 while allowing relative rotation between drive shaft 70 and elongate dilator body 20.

Drive shaft 70 includes a cylindrical transmission portion 75 projecting axially distally at distal end 70a. Transmission portion 75 has a diameter less than the diameter of second distal cylindrical portion 72. An exterior transverse surface 76 extends radially between second distal cylindrical portion 72 and cylindrical transmission portion 75. As shown in FIGS. 7A and 7B, exterior transverse surface 76 includes a hole 77 formed therein for receipt of another portion of torsion spring 80, as will be described. Cylindrical transmission portion 75 comprises a pair of opposed cooperative inclined force transmission surfaces 78a and 78b that are configured to cooperate with inclined force transmission surfaces 37a and 37b on elongate sleeve 30 to axially move elongate sleeve 30 within central lumen 21 of elongate dilator body 20, as will be described.

Referring now to FIGS. 8A through 8C, details of torsion spring 80 are described. Torsion spring 80, conventionally formed in a cylindrical configuration, has a distal end 80a, a proximal end 80b, a central axis 80c and a lumen 81 defining an inner diameter 82. Torsion spring 80 has a first connecting post 83 projecting axially distally from distal end 80*a* and a second connecting post 84 projecting axially distally from proximal end 80*b*. Inner diameter 82 is configured to receive second proximal cylindrical portion 33 of elongate sleeve 30 through distal end 80*a*. Upon such receipt, first connecting post 83 is received in hole 65 of keying ring 60 with distal end 80*a* of torsion spring contacting proximal end 60*b* of keying ring 60. Inner diameter 82 is further configured to receive cylindrical transmission portion 75 through proximal end 80*b*. Upon such receipt, second connecting post 84 is received in hole 77 formed in exterior transverse surface 76 of cylindrical transmission portion 75. With keying ring 60 being keyed to elongate sleeve 30, torsion spring 80 is effectively captured between elongate sleeve 30 and drive shaft 70. Torsion spring 80 is configured to hold a fixed radial position of control knob 90 relative to elongate dilator body 20, as will be described. In a particular arrangement, torsion spring 80 is formed as a right-hand wound spring and is configured such that in a relaxed condition, connecting posts 83 and 84 are aligned rotationally within a few degrees of each other. As such, if torsion is applied to spring 80 in a counterclockwise direction, spring 80 will tend to contract. As post 83 and 84 deviate counterclockwise with respect to each other radially torque is created, which tends to return torsion spring 80 inherently back to its relaxed state. If torsion is applied to torsion spring 80 in a clockwise direction when it is in its relaxed state, it will tend to expand. As post 83 and 84 deviate clockwise with respect to each other radially torsional forces tending to return to its relaxed state will be created.

Turning now to FIGS. 9A through 9E, details of control knob 90 now described. Control knob 90 has a distal end 90*a*, a proximal end 90*b*, an outer cylindrical surface 90*c*, and a lumen 91 extending therethrough. Lumen 91 is defined by inner cylindrical surface 90*d* and has a diameter that is sized and configured to sliding receive first proximal cylindrical portion 71 of drive shaft 70. Lumen 91 is truncated by an internal flat surface 92 extending for a length within lumen 91. When first proximal cylindrical portion 71 of drive shaft 70 is received within lumen 91 of control knob 90, internal flat surface 92 will contact flat surface 73 of drive shaft 70 thereby positioning control knob 90 in a keyed disposition relative to drive shaft 70. In such keyed disposition, rotational movement between control knob 90 and drive shaft 70 is prevented while relative axial movement therebetween is allowed.

Control knob 90 comprises a series of radial cuts 93 extending into outer cylindrical surface 90*c* adjacent distal end 90*a*. Each of radial cuts 93 is formed as an arcuate recess and is sized and configured to receive control pin 101 for holding an axial position of control knob 90 relative to dilator body 20, as will be described. Radial cuts 93 extend along outer cylindrical surface 90*c* for an axial length therealong from distal end 90*a* toward proximal end 90. Radial cuts 93 extend radially around a portion of the circumference of outer cylindrical surface 90*c*. In a particular arrangement, radial cuts 93 may extend in a circumferential arc of approximately 100°, which has been found to be sufficient to enable proper projection of docking teeth 31 from the distal end 20*a* of elongate dilator body 20 while maintaining control pin 101 in a selected radial cut 93. It should be appreciated, however, that a circumferential arc of other angular extents may be considered. Control knob 90 comprises an exterior flat surface 94 formed axially along outer cylindrical surface 90*c* for at least the axial length of radial cuts 93, with exterior flat surface 94 being in communication with said radial cuts 93.

Control knob 90 may have a series depth markings 95 located adjacent proximal end 90*b* to aid the user in determining the proper depth of a drill or tap to be used with drill tap dilator 10. Proximal end 90*b* may also have a knurled surface 96 in a manner to enhance gripping of control knob for rotational and sliding movement relative to elongate dilator body 20. Control knob 90 has a circular entrance opening 97 formed through proximal end 90*b* as shown in FIG. 9E in communication with lumen 91, entrance opening 97 having a diameter substantially the same as the diameter of lumen 30*c* of elongate sleeve 30 and circular exit opening 23 for clearance of an entry dilator, as will be described.

Having described the details of the components of drill tap dilator 10, the assembly and functioning of drill tap dilator 10 are now described. FIGS. 1 and 10A through 10C illustrate drill tap dilator 10 with docking teeth 31 being in a retracted position. Referring also to FIG. 2B a subassembly 11 is initially formed as shown with compression spring 40 being introduced onto first distal cylindrical portion 32 of elongate sleeve 30, keying sleeve 60 being placed onto second proximal cylindrical portion 33 and connecting posts 83 and 84 of torsion spring 80 being inserted respectively into holes 65 of keying ring 60 and 77 of drive shaft 70. Subassembly 11 is introduced into lumen 21 of elongate dilator body 20 until distal end 40*a* of compression spring 40 engages shoulder 28 extending transversely within lumen 21. Continued axial introduction of subassembly 11 compresses compression spring 40 captured between shoulder 28 and exterior transverse surface 34 of elongate sleeve 30. With compression spring 40 in compression guide pin 50 is inserted through slot 29 of elongate dilator body 20 and into opening 35 of elongate sleeve 30 with guide pin 50 being suitably secured therein, such as by spot welding.

Figure 10C:
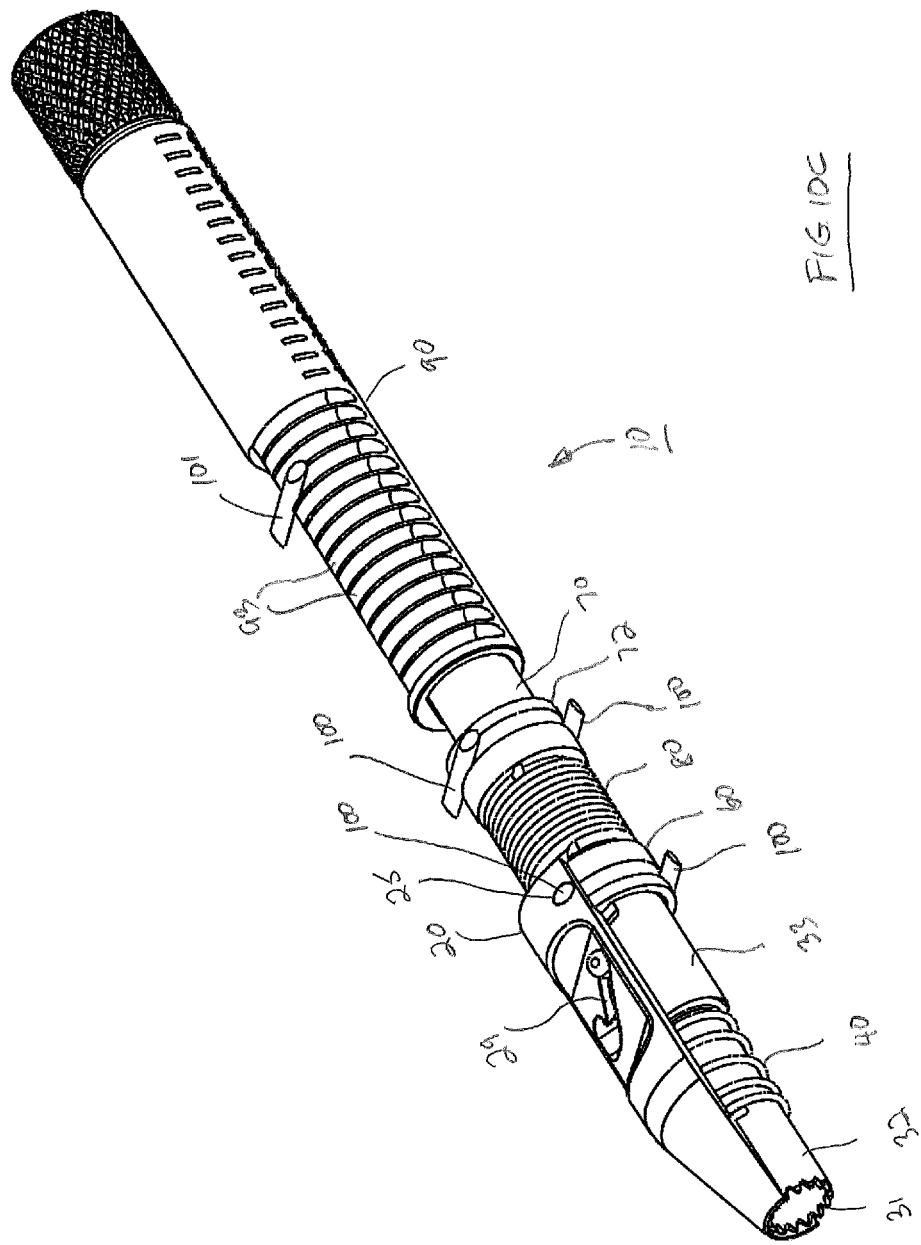

With compression spring 40 being in compression, guide pin 50 is urged axially proximally such that guide pin 50 is located in the proximal-most portion of slot 29 and docking teeth 31 are in a retracted position within lumen 21 of elongate dilator body 20, as shown in FIGS. 10A, 10B and 10C. A first pair of pins 100 is introduced into and secured in holes 25 and into recess 67 of keying ring 60 to axially hold the position of keying ring 60 relative to elongate dilator body 20 while allowing relative rotation between keying ring 60 and elongate dilator body 20. As noted above, while keying ring 60 is axially affixed relative to elongate dilator body 20, elongate sleeve 30 with docking teeth 31 thereon may move axially under the force of compression spring 40. Thereafter, a second pair of pins 100 is introduced into and secured such as by spot welding in holes 26 and into recess 74 of drive shaft 70 to axially hold the position of drive shaft 70 relative to elongate dilator body 20 while allowing relative rotation between drive shaft 70 and elongate dilator body 20.

Control knob 90 is then introduced into lumen 21 of elongate dilator body 20 onto drive shaft 70 with internal flat surface 92 of knob 90 being aligned with exterior flat surface 73 of drive shaft 70. Such orientation as noted above will place control knob 90 in a keyed disposition relative to drive shaft 70. In such keyed disposition, rotational movement between control knob 90 and drive shaft 70 is prevented while relative axial movement therebetween is allowed. As such, drive shaft 70 and control knob 90 rotate together. Relative axial movement allows adjustment of the length of drill tap dilator 10, as will be described. Various axial positions of control knob 90 relative to elongate dilator body 20 are tentatively fixed by control pin 101 which is introduced into and secured in holes 27 and into a selected one of radial cuts 93 of control knob 90. As assembled, all the lumens of the constituent components of tap dilator 10 described above are in axial alignment and communication and together with entrance opening 97 and exit opening 23 define a passageway 102 (see FIG. 17) for passage through drill tap dilator 10 of an entry dilator, as will be described.

Figure 11B:
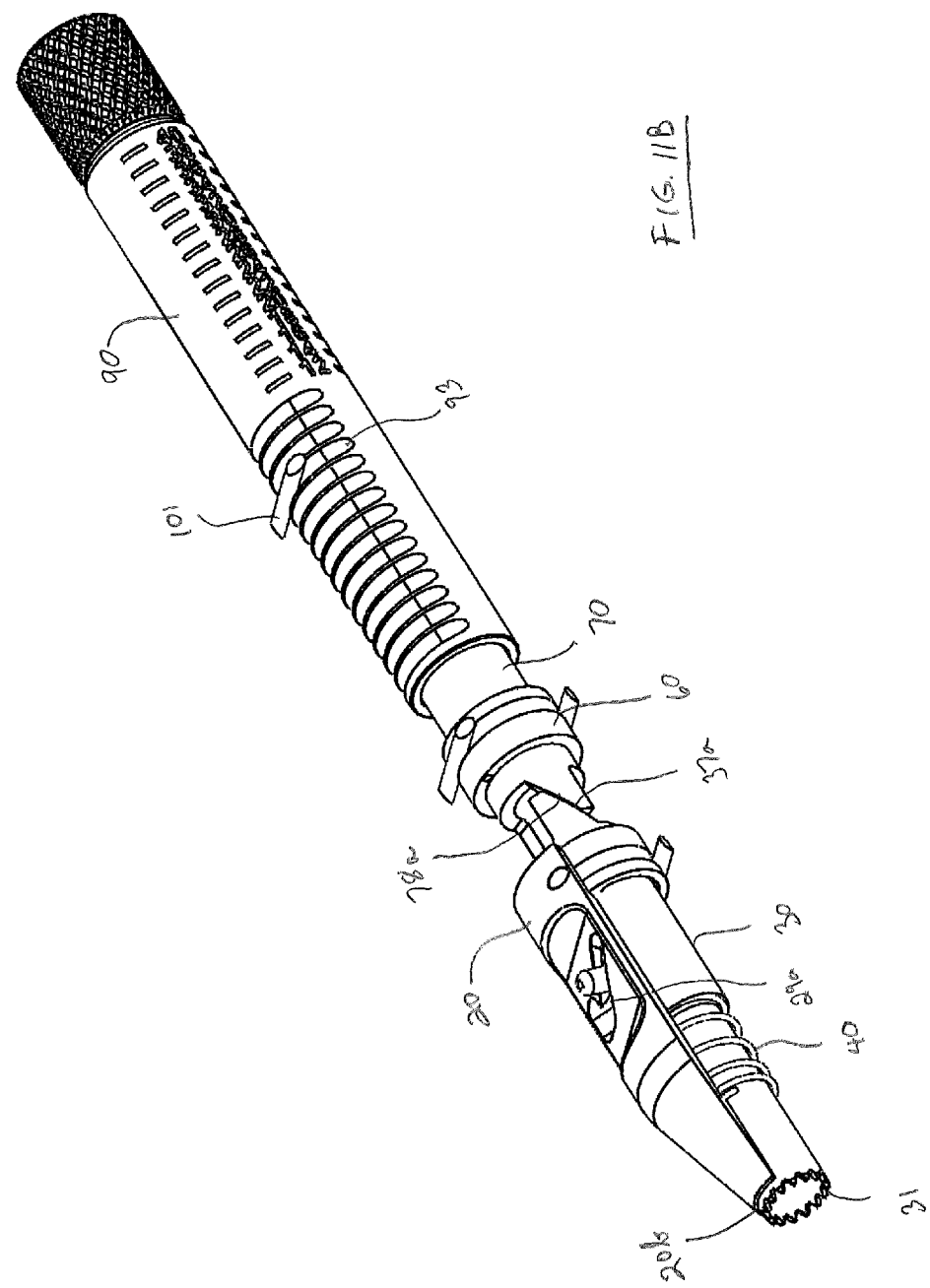
FIG. 11B is the view of the drill tap dilator of FIG. 11A showing a cutaway portion to reveal details of internal components in the intermediate position.

Turning now to FIGS. 11A and 11B, a description of the operative functions involved in causing docking teeth 31 to project distally from the distal end 20b of drill tap dilator 10 is provided. In FIG. 10C docking teeth are in a retracted position. In this retracted position connecting posts 83 and 84 of torsion spring 80 are respectively located into holes 65 of keying ring 60 and 77 of drive shaft 70 with connecting posts 83 and 84 being radially offset about 25° from each other. Thus, torsion spring 80 is slightly loaded and applies some torsion to drive shaft 70. From a first rotational position as shown in FIG. 10C, control knob 90 is rotated in a clockwise direction relative to elongate dilator body 20. During such rotational movement drive shaft 70 will likewise be rotated clockwise. During this rotational movement control pin 101 will remain within the same radial cut 93 as described and shown above with respect to FIG. 10C. Also, during this clockwise rotation of control knob 90, the torsional load on spring 80 is reduced allowing torsion spring 80 to be rotated clockwise with drive shaft 70 and keying ring 60. Further, during such clockwise rotation of control knob 90 inclined force transmission surfaces 37a and 37b of elongate sleeve 30 engage cooperative inclined force transmission surfaces 78a and 78b of drive shaft 70 to axially move elongate sleeve 30 in the distal direction from the axial position shown in FIG. 10C within central lumen 21 of elongate dilator body 20 against the compression force of compression spring 40. This axial movement of elongate sleeve 30 causes docking teeth 31 to partially project axially from the distal end 20b. Additionally, guide pin 50 during the distal axial movement of elongate sleeve 30 slides within first extent 29a of slot 29 to an intermediate position as shown in FIG. 11B. It should be appreciated that while elongate sleeve 30 will move axially distally relative to elongate dilator body 20 during clockwise rotation of control knob 90, there will also be some slight angular movement of elongate sleeve 30 within elongate dilator body 20.

Continued clockwise rotation of control knob 90 to a second rotational position relative to elongate dilator body 20 will cause further axial movement of elongate sleeve 30 within central lumen 21 of elongate dilator body to a further axial position as shown in FIGS. 12A and 12B as inclined force transmission surfaces 37a and 37b of elongate sleeve 30 continue to engage cooperative inclined force transmission surfaces 78a and 78b of drive shaft 70. With control knob 90 in a second rotational position guide pin 50 will reach the distalmost end of slot first extent 29b and docking teeth 31 will project axially a maximum extent beyond the distal end 20b of elongate dilator body 20. During this further clockwise rotation of control knob 90 the radial extent of such rotation is less than the arc about which radial cut 93 is formed. As such, control pin 101 will continue to remain within the selected radial cut 93 during the entire clockwise rotation of control knob 90 sufficient to fully project docking teeth 31 outwardly from elongate dilator body 20.

Once guide pin 50 reaches the distalmost end of first extent 29a of slot 29 guide pin 50 will be axially aligned with second extent 29b, which defines a hooked opening, as described above. At this point, with the torque from torsion spring 80 being minimal guide pin 50 under the force applied by compression spring 40 will be urged in the proximal direction into the hooked opening of slot second extent 29b, as shown in FIGS. 13A and 13B. The movement of guide pin 50 into the hooked opening will cause a slight retraction of elongate sleeve 30 with docking teeth 31 thereon in the proximal direction. Nevertheless, docking teeth 31 will project axially beyond the distal end 20b elongate dilator body 20 a sufficient amount to penetrate into the bone of a cervical vertebra.

Figure 16:
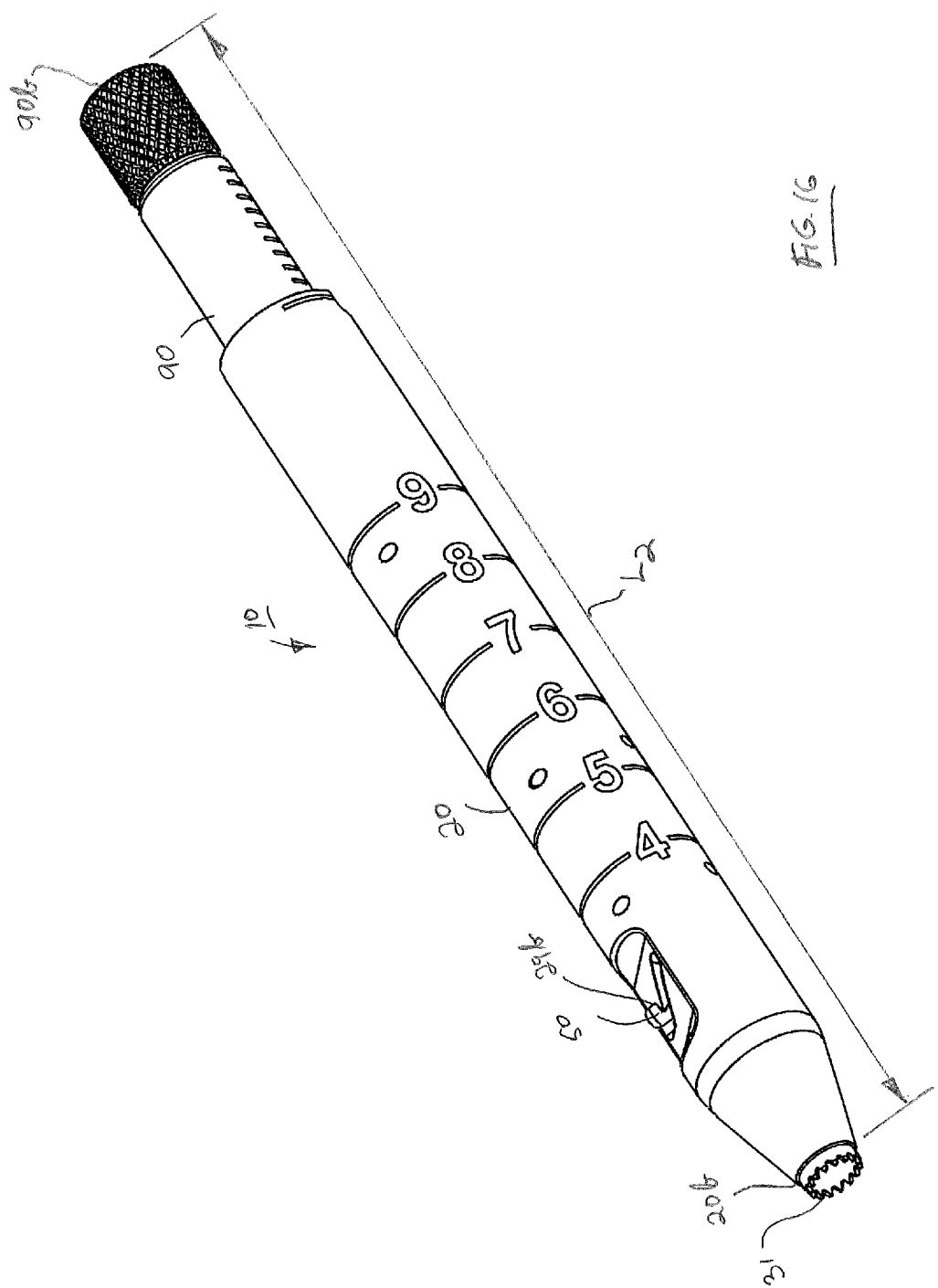
FIG. 16 is a perspective view of the drill tap dilator showing the increase in the overall length of the drill tap dilator from FIG. 15.

Having described the functional movement of drill tap dilator 10 to effect axial distal projection of docking teeth 31, a description of an adjustment of the length of drill tap dilator 10 is now provided by reference to FIGS. 14 through 16. With guide pin 50 disposed in hooked opening of slot second extent 29b, keyed ring 60, elongate sleeve 30 and hence docking teeth 31 are effectively locked against movement relative to elongate dilator body 20. In this position, control knob 90 is in the second rotational position relative to elongate dilator body 20. From this second rotational position shown in FIG. 13B control knob 90 may be rotated in a counterclockwise direction to a third rotational position shown in FIG. 14 thereby applying a torsional force against torsion spring 80. Drive shaft 70 will likewise be rotated in a counterclockwise direction. During such counterclockwise rotation of control knob 90 with elongate sleeve 30 and keying ring 60 being held against movement as described above, inclined force transmission surfaces 37a and 37b of elongate sleeve 30 separate from cooperative inclined force transmission surfaces 78a and 78b of drive shaft 70, as shown in FIG. 15.

Further, during such counterclockwise rotation of knob 90 control pin 101 is moved out from the selected radial cut 93 and into juxtaposition with flat surface 94, as shown in FIG. 14. This allows control knob 90 to be freely axially moved from a first axial position along drive shaft 70 to a different second axial position whereby control pin 101 is aligned for receipt into a second selected radial cut 93', as shown in FIG. 15. Upon alignment of control pin 101 and second selected radial cut 93', the torsional force in the counterclockwise direction may be released. This allows torsion spring 80 to inherently return to its normal state, thereby causing control knob 90 to rotate back clockwise to its second rotational position relative to elongate dilator body 20 and thereby cause control pin 101 to be received in second selected radial cut 93'. As such, the length of drill tap dilator 10, defined as the distance between distal end 20b of dilator body 20 and proximal end 90b of control knob 90, may be adjusted from a first length $L_1$ as shown in FIG. 13A to a second length $L_2$ as shown in FIG. 16. It should be appreciated that the length of drill tap dilator 10 may be adjusted independently of the extension of docking teeth 31. As such, control knob 90 may be rotated in a counterclockwise direction with docking teeth 31 in the retracted position and control knob 90 being in the first rotational position of FIG. 10C to the third rotational position of FIG. 14.

To facilitate removal of drill tap dilator 10 from the surgical site upon completion of a surgical procedure, docking teeth 31 are retracted. To retract docking teeth 31 for further use from the position shown in FIG. 16. to the position shown in FIG. 1 guide pin 50 is manually moved. Guide pin 50 is first manually urged in the distal direction of the hook opening along extent 29b to overcome the force of compression spring 40. A counterclockwise force is then applied to guide pin 50 to move it back into the first extent 29a. From this position, compression spring 40 will urge guide pin 50 and thereby elongate sleeve 30 back to the position shown in FIG. 1.

Figure 17:
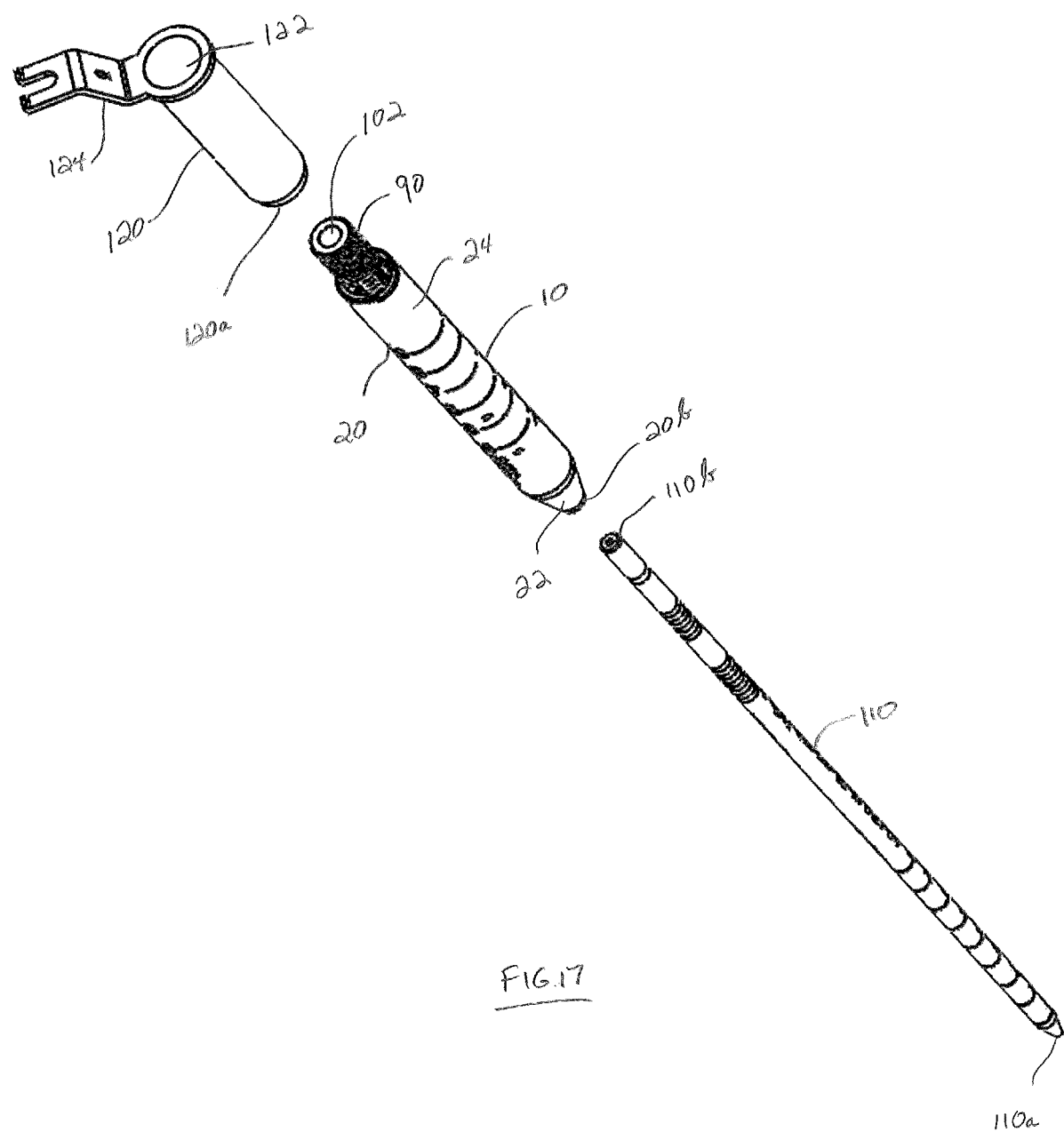
FIG. 17 is an exploded perspective view showing the drill tap dilator of the subject invention positioned for use with an outer rigid arm dilator and an entry dilator.

Having described the structure and function of the subject drill tap dilator 10 herein, an exemplary method of using drill tap dilator 10 is now described. For example, drill tap dilator 10 may be used in the minimally invasive placement of screws for spinal fixation in cervicothoracic stabilization surgery using a posterior access. Using fluoroscopy, a posterior trajectory to the lateral mass of a cervical vertebral body may be established and an incision is made through the skin of the patient for an access path to the surgical site. An entry dilator 110 as shown in FIG. 17 may then be introduced into the incision and through tissue down to the targeted location on the cervical body lateral mass. Entry dilator 110 typically is of length such that while the distal end 110a is in contact with the targeted lateral mass, the proximal end 110b extends outwardly exteriorly beyond the skin of the patient. With docking teeth 31 being in the retracted position of FIG. 1 as described above, drill tap dilator 10 is introduced over entry dilator 110 with entry dilator 110 passing fully through passageway 102 of drill tap dilator 10. As drill tap dilator 10 passes through the incision, tapered surface 22 drill tap dilator 10 dilates tissue until distal end 20b contacts the targeted lateral mass. During insertion, with docking teeth 31 being in a retracted position, trauma to surrounding tissue is minimized. At this point control knob 90 is rotated clockwise to extend docking teeth 31 causing docking teeth 31 to penetrate into the targeted lateral mass and dock drill tap dilator 10 onto the bone surrounding the intended surgical site. As such, the location of the intended surgical site may be maintained for the preparation of a hole in the targeted lateral mass for the insertion of a lateral mass screw.

Figure 18:
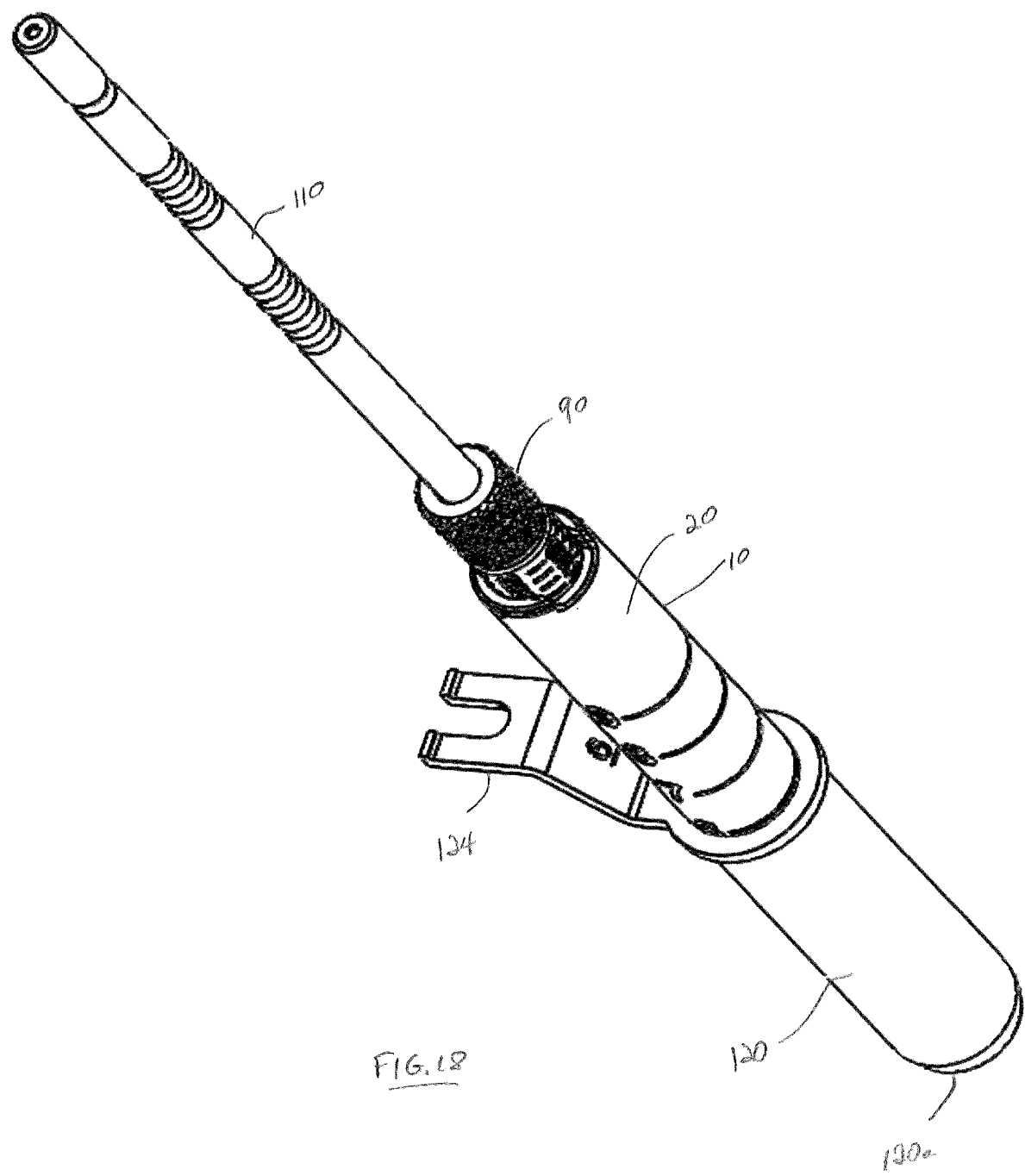
FIG. 18 is a perspective view of the drill tap dilator of the subject invention in use with the outer rigid arm dilator and entry dilator of FIG. 17.

An outer rigid arm dilator 120 as shown in FIG. 17 is then placed over drill tap dilator 10 as shown in FIG. 18 and into the dilated tissue until the distal end 120a of rigid arm dilator 120 is adjacent the intended surgical site. As noted above, outer cylindrical surface 24 of elongate dilator body 20 has an outer diameter that is sized to mate with an interior opening 122 of outer rigid arm dilator 120. Outer rigid arm dilator 120 includes a mounting bracket 124 which can be fastened to a flexible support arm which is mounted on a surgical table and adjustable into a fixed position to provide firm support for outer rigid arm dilator 120. At this point in the procedure, entry dilator 110 may be removed.

Under fluoroscopy, the depth to which a lateral mass screw may be introduced into the lateral mass is determined by the surgeon. With drill tap dilator 10 being docked on the cervical vertebral body, the length of the drill tap dilator 10 is suitably adjusted as described hereinabove by rotating control knob 90 counterclockwise and manually axially moving control knob 90 to a desired position for the appropriate depth of the lateral mass screw. As shown in FIG. 19, depth markings 95 on control knob 90 as referenced by undercut 20d of elongate dilator body 20 may aid the user in determining the proper depth of a drill or tap to be used with drill tap dilator 10. FIG. 20 shows a drill 130 that may be used with drill tap dilator 10. Drill 130 includes an elongate shaft 132 having a distal end 130a and a proximal end 130b. Proximal end 130b may include a feature for connection to a suitable external tool for rotating drill 130. A stop 134 is included on shaft 132 adjacent proximal end 130b. A drill bit 136 projects axially from distal end 132a of drill 130. Having established the desired depth to which a lateral mass screw may be inserted into the targeted lateral mass, drill 130 is introduced through the passageway 102 of drill tap dilator until stop 134 engages the proximal end 90b control knob 90, as shown in FIG. 19. With the desired screw depth having been established by drill tap dilator 10 by adjustment of the length as described above, engagement of drill stop 134 with control knob proximal end 90b, which serves as a stop face, will result in drill bit 136 projecting axially beyond the distal end 20a of elongate dilator body 20 a distance, D that is the desired depth. Upon drilling the hole in the targeted lateral mass to the appropriate depth, a tap formed similar to drill 130 may then be used in conjunction with drill tap dilator 10 to threadably tap the hole formed by drill tip 136.

At this point in the procedure drill tap dilator 10 may be removed from outer rigid arm dilator 120, with outer rigid arm dilator 120 remaining in place. A lateral mass screw may then be introduced through interior opening 122 of outer rigid arm dilator 120 and threadably inserted into the tapped hole formed in the targeted lateral mass. It should be appreciated that a similar procedure may be followed where a pedicle screw is intended to be posteriorly inserted into the pedicle of a cervical vertebral body.

The subject drill tap dilator 10 has one control knob 90 that aids in both stop length adjustment and for the deployment of docking teeth 31. Having both features in the same instrument eliminates the need for swapping dilators and allows all bone work preparation to be done with one dilator. This reduces potential for error and potential loss of the surgical site during the procedure.

While the invention has been illustrated and described in detail in the drawings and foregoing description, the same should be considered as illustrative and not restrictive in character. As such, it is understood that only the preferred embodiments have been presented and that all changes, modifications and further applications that come within the spirit of the invention are desired to be protected.

What is claimed is:

1. A drill tap dilator, comprising:
   an elongate dilator body having a distal end, a proximal end and a central lumen extending therethrough along a longitudinal axis;
   an elongate sleeve configured for receipt within said central lumen and having a distal end, a proximal end and a lumen extending therethrough, said elongate sleeve having docking teeth at the distal end thereof, said elongate sleeve being axially movable from a first position wherein said teeth are retracted within said central lumen to a second position wherein said teeth project distally beyond said distal end of said dilator body, and
   an elongate control knob having a distal end and a proximal end, said control knob being coupled to said sleeve and movable relative to said elongate dilator body, said control knob being configured upon movement relative to said elongate dilator body to move said elongate sleeve from said first position to said second position and to allow adjustment of a length of said drill tap dilator between the distal end of said dilator body and the proximal end of said control knob.

2. The drill tap dilator of claim 1, wherein said control knob is configured to move rotationally relative to said elongate dilator body to move said elongate sleeve from said first position to said second position, and wherein said control knob is configured to move axially relative to said elongate dilator body to allow said length adjustment of said drill tap dilator.

3. The drill tap dilator of claim 2, wherein said control knob is coupled to said elongate sleeve by an elongate drive shaft, said drive shaft having a distal end, a proximal end and a lumen extending therethrough.

4. The drill tap dilator of claim 3, wherein said drive shaft is fixed to said elongate dilator body in a manner to prevent relative axial movement but to allow relative rotational movement therebetween.

5. The drill tap dilator of claim 4, wherein said control knob has a lumen extending therethrough, said control knob lumen being configured to receive said drive shaft therewithin, said drive shaft being keyed with an interior surface within said control knob lumen to allow joint rotation of said control knob and said drive shaft while allowing said control knob to move axially on said drive shaft.

6. The drill tap dilator of claim 5, wherein said proximal end of said elongate sleeve comprises an inclined force transmission surface and said distal end of said drive shaft comprises a cooperative inclined force transmission surface, said inclined force transmission surface and said cooperative inclined force transmission surface being engaged in a manner such that upon rotation of said drive shaft said elongate sleeve is moved axially distally relative to said dilator body.

7. The drill tap dilator of claim 6, wherein said elongate dilator body comprises a cylindrical outer surface and has a slot adjacent said distal end thereof extending through said outer cylindrical surface and into said central lumen, said slot extending at an angle relative to said longitudinal axis, and wherein said elongate sleeve supports a guide pin extending in said slot and movable therein upon axial movement of said elongate sleeve.

8. The drill tap dilator of claim 7, further including a compression spring captured in a compressed condition between an internal surface of said dilator body and an exterior surface of said elongate sleeve to tentatively hold said elongate sleeve in said first position.

9. The drill tap dilator of claim 8, further comprising a torsion spring captured between said drive shaft and said elongate sleeve, said torsion spring being configured to control the rotational movement of said control knob relative to said dilator body.

10. A drill tap dilator, comprising:
an elongate dilator body having a distal end, a proximal end and a central lumen extending therethrough along a longitudinal axis;
an elongate sleeve configured for receipt within said central lumen and having a distal end, a proximal end and a lumen extending therethrough said sleeve having docking teeth at the distal end and being axially movable from a first position wherein said teeth are retracted within said central lumen to a second position wherein said teeth project distally beyond said distal end of said dilator body,
a biasing element configured to normally bias said sleeve in said first position; and
an elongate control knob coupled to said sleeve and movable relative to said dilator body to overcome said normal bias and move said sleeve to said second position.

11. The drill tap dilator of claim 10, wherein said biasing element is captured in a compressed condition between a shoulder extending transversely within said central lumen of said elongate dilator body and an exterior transverse surface on said elongate sleeve to tentatively hold said elongate sleeve and said first position.

12. The drill tap dilator of claim 11, wherein said biasing element is a cylindrical compression spring having an inner diameter and an outer diameter, and wherein said elongate sleeve comprises a first distal cylindrical portion and a second proximal cylindrical portion, said first distal cylindrical portion having a diameter less than a diameter of said second proximal cylindrical portion, said exterior transverse surface extending radially between said first distal cylindrical portion and said second proximal cylindrical portion, said compression spring being located on said first distal cylindrical portion.

13. The drill tap dilator of claim 12, wherein said elongate dilator body comprises a tapered surface extending from said distal end and tapering outwardly to an outer cylindrical surface of said elongate dilator body.

14. The drill tap dilator of claim 13, wherein said elongate dilator body has a slot adjacent said distal end thereof extending through said outer cylindrical surface and into said central lumen, said slot having a first extent extending at an angle relative to said longitudinal axis.

15. The drill tap dilator of claim 14, wherein said elongate sleeve supports a guide pin extending in said slot and movable upon axial movement of said elongate sleeve within said first extent of said slot.

16. The drill tap dilator of claim 15, wherein said slot further comprises a second extent at a distalmost end of said slot extending proximally in an axial direction, said guide pin being movable by a biasing force from said compression spring into said second extent upon said guide pin being moved to said distalmost end of said first extent.

17. A drill tap dilator, comprising:
an elongate dilator body having a distal end, a proximal end and a central lumen extending therethrough along a longitudinal axis;
an elongate sleeve configured for receipt within said central lumen and having a distal end, a proximal end and a lumen extending therethrough, said sleeve having docking teeth at the distal end and being axially movable from a first position wherein said teeth are retracted within said central lumen to a second position wherein said teeth project distally beyond said distal end of said dilator body, and
an elongate control knob coupled to said sleeve and movable relative to said dilator body in two opposite rotational directions, movement of said control knob in a first rotational direction causing said sleeve to move from said first position to said second position and movement of said control knob in a second opposite rotational direction allowing said control knob to move axially relative to said dilator body to thereby adjust a length of said drill tap dilator.

18. The drill tap dilator of claim 17, wherein said control knob has a distal end, a proximal end, an outer cylindrical surface and a lumen extending therethrough, and wherein said control knob comprises a series of radial cuts extending into said outer cylindrical surface adjacent the distal end of said control knob, said radial cuts extending for an axial length therealong and radially around a portion of the circumference of said control knob.

19. The drill tap dilator of claim 18, wherein said control knob comprises a flat surface extending axially along the outer surface of said control knob for at least the axial length of said radial cuts, said flat surface being in communication with said radial cuts.

20. The drill tap dilator of claim 19, wherein said control knob is coupled to said elongate sleeve by an elongate drive shaft, said drive shaft having a distal end, a proximal end and a lumen extending therethrough.

21. The drill tap dilator of claim 20, wherein said drive shaft is fixed to said elongate dilator body in a manner to prevent relative axial movement but to allow relative rotational movement therebetween.

22. The drill tap dilator of claim 21, wherein said elongate dilator body supports a control pin extending transversely relative to said longitudinal axis, said control pin being configured to be selectively received in a first cut of said series of radial cuts with said control knob being in a first axial position to prevent axial movement of said control knob relative to said drive shaft and thereby relative to said elongate dilator body.

23. The drill tap dilator of claim 22, further comprising a torsion spring captured between said drive shaft and said elongate sleeve, said torsion spring applying a normal torsional force to tentatively hold said control knob in a first rotational position relative to said elongate dilator body.

24. The drill tap dilator of claim 23, wherein said torsion spring is configured such that upon rotation of said control knob in said first rotational direction from said first rotational position to a second rotational position relative to said elongate dilator body no torsional force is applied to said torsion spring such that during said rotation said torsion spring rotates with said control knob and said drive shaft to axially move said elongate sleeve from said first position to said second position.

25. The drill tap dilator of claim 24, wherein said torsion spring is configured such that upon rotation of said control knob in said second opposite rotational direction from said first rotational position to a third rotational position relative to said elongate dilator body a torsional force is applied to said torsion spring to overcome said normal torsional force allowing said control knob to rotate relative to said elongate dilator body such that said control pin is moved out from said first radial cut and into juxtaposition with said flat surface of said control knob which allows said control knob to be axially moved along said drive shaft to a second axial position whereby said control pin is aligned for receipt into a second radial cut of said series of radial cuts.

26. The drill tap dilator of claim 25, wherein said torsion spring is configured such that upon release of said torsional force in said second opposite rotational direction, said torsion spring will inherently cause said control knob to rotate back to said first rotational position relative to said elongate dilator body and thereby cause said control pin to be received in said second radial cut.

* * * * *